US008282918B2

(12) United States Patent
Wold et al.

(10) Patent No.: US 8,282,918 B2
(45) Date of Patent: Oct. 9, 2012

(54) POLYNUCLEOTIDES ENCODING RPA4/RPA32 HYBRID POLYPEPTIDES

(75) Inventors: Marc S. Wold, Iowa City, IA (US); Stuart J. Haring, West Fargo, ND (US)

(73) Assignee: University of Iowa Research Foundation, Iowa City, IA (US)

( * ) Notice: Subject to any disclaimer, the term of this patent is extended or adjusted under 35 U.S.C. 154(b) by 178 days.

(21) Appl. No.: 12/671,356

(22) PCT Filed: Jul. 29, 2008

(86) PCT No.: PCT/US2008/071421
§ 371 (c)(1),
(2), (4) Date: May 11, 2010

(87) PCT Pub. No.: WO2009/018250
PCT Pub. Date: Feb. 5, 2009

(65) Prior Publication Data
US 2010/0227392 A1 Sep. 9, 2010

Related U.S. Application Data

(60) Provisional application No. 60/952,687, filed on Jul. 30, 2007.

(51) Int. Cl.
*A01N 63/00* (2006.01)
*C12N 15/00* (2006.01)
*C07H 21/02* (2006.01)
*C07H 21/04* (2006.01)

(52) U.S. Cl. ............... 424/93.21; 424/93.2; 435/320.1; 536/23.1; 536/23.5; 536/24.1

(58) Field of Classification Search .............. 424/93.2, 424/93.21; 435/320.1; 536/23.1, 23.5, 24.1
See application file for complete search history.

(56) References Cited

U.S. PATENT DOCUMENTS

| | | | |
|---|---|---|---|
| 4,970,154 | A | 11/1990 | Chang |
| 5,399,346 | A | 3/1995 | Anderson et al. |
| 5,593,875 | A | 1/1997 | Wurm et al. |
| 5,631,236 | A | 5/1997 | Woo et al. |
| 5,635,399 | A | 6/1997 | Kriegler et al. |
| 5,672,344 | A | 9/1997 | Kelley et al. |
| 5,676,954 | A | 10/1997 | Brigham |
| 5,679,559 | A | 10/1997 | Kim et al. |
| 7,094,891 | B1 | 8/2006 | Alaoui-Jamali et al. |

FOREIGN PATENT DOCUMENTS

WO 9640958 12/1996

OTHER PUBLICATIONS

Takagi et al., 2005, N_Geneseq Accession No. AED22254, computer printout pp. 12-14.*
Erdile et al., 1990, The Journal of Biological Chemistry, vol. 265, No. 6, pp. 3177-3182.*
Erdile et al., GenEmbl Accession No. J05249, computer printout pp. 24-25.*
Erdile et al., "The Primary Structure of the 32-kDa Subunit of Human Replication Protein A", Journal of Biological Chemistry, Feb. 25, 1990, 265(6):3177-3182.
Erdile et al., "Characterization of a cDNA Encoding the 70-kDa Single-stranded DNA-binding Subunit of Human Replication Protein A and the Role of the Protein in DNA Replication", Journal of Biological Chemistry, Jun. 25, 1991, 266(18):12090-12098.
Givalos et al., "Replication protein A is an independent prognostic indicator with potential therapeutic implications in colon cancer", Modern Pathology, 2007, 20:159-166.
Haring et al., "A naturally occurring human RPA subunit homolog does not support DNA replication or cell-cycle progression", Nucleic Acids Research, 2010, 38(3):846-858.
Keshav et al., "Rpa4, a Homolog of the 34-Kilodalton Subunit of the Replication Protein A Complex", Molecular and Cellular Biology, Jun. 1995, 15(6):3119-3128.
Mason et al., "An Alternative Form of Replication Protein A Prevents Viral Replication in Vitro", Journal of Biological Chemistry, Feb. 20, 2009, 284(8):5324-5331.
Nagelhust et al., "A Sequence in the N-terminal Region of Human Uracil-DNA Glycosylase with Homology to XPA Interacts with the C-terminal Part of the 34-kDa Subunit of Replication Protein A", Journal of Biological Chemistry, Mar. 7, 1997, 272(10):6561-6566.
Pfaffl, "A new mathematical model for relative quantification in real-time RT-PCR", Nucleic Acids Research, 2001, 29(9):2002-2007.
Singh et al., "The 32 kDa subunit of replication protein A (RPA) participates in the DNA replication of Mung bean yellow mosaic India virus (MYMIV) by interacting with the viral Rep protein", Nucleic Acids Research, Dec. 20, 2006, 35(3):755-770.
Tomkiel et al., "Autoimmunity to the Mr 32,000 Subunit of Replication Protein A in Breast Cancer", Clinical Cancer Research, Mar. 2002, 8:752-758.
Umbricht et al., "Cloning, Overexpression, and Genomic Mapping of the 14-kDa Subunit of Human Replication Protein A", Journal of Biological Chemistry, Mar. 25, 1993, 268(9):6131-6138.
International Search Report for PCT/US2008/071421 dated Feb. 23, 2009. Written Opinion for PCT/US2008/071421 dated Feb. 23, 2009.
Bartos et al., "Catalysis of Strand Annealing by Replication Protein A Derives from Its Strand Melting Properties", Journal of Biological Chemistry, Aug. 1, 2008, 283(31):21758-21768.
Binz et al., "The Phosphorylation Domain of the 32-kDa Subunit of Replication Protein A (RPA) Modulates RPA-DNA Interactions", Journal of Biological Chemistry, Sep. 12, 2003, 278(37):35584-35591.
Binz et al., "Functional Assays for Replication Protein A (RPA)", Methods in Enzymology, 2006, 409:11-38.

(Continued)

*Primary Examiner* — Shin-Lin Chen
(74) *Attorney, Agent, or Firm* — Andrus, Sceales, Starke & Sawall, LLP

(57) ABSTRACT

Disclosed are polynucleotides and polypeptides that are useful for assessing and modulating cell proliferation. The polynucleotides may comprise coding regions for RPA4 and RPA4/RPA32 hybrid polypeptides. The polynucleotides may be used in gene vectors for modulating cell proliferation in a patient in need thereof. Diagnostic methods related to assaying RPA4 expression in test samples in order to detect proliferating or cancerous cells also are disclosed.

13 Claims, 22 Drawing Sheets

OTHER PUBLICATIONS

Binz et al., "Regulatory Functions of the N-terminal Domain of the 70-kDa Subunit of Replication Protein A (RPA)", Journal of Biological Chemistry, Aug. 1, 2008, 283(31):21559-21570.

Chan et al., "Purification and Characterization of ATM from Human Placenta", Journal of Biological Chemistry, Mar. 17, 2000, 275(11):7803-7810.

Cho et al., "RBT1, a novel transcriptional co-activator, binds the second subunit of Replication Protein A", Nucleic Acids Research, 2000, 28(18):3478-3485.

Daughdrill et al., "The weak interdomain coupling observed in the 70 kDa subunit of human replication protein A is unaffected by ssDNA binding", Nucleic Acids Research, 2001, 29(15):3270-3276.

Daughdrill et al., "Chemical shift changes provide evidence for overlapping single-stranded DNA- and XPA-binding sites on the 70 kDa subunit of human replication protein A", Nucleic Acids Research, 2003, 31(14):4176-4183.

Deng et al., "Structure of the Full-length Human RPA14/32 Complex Gives Insights into the Mechanism of DNA Binding and Complex Formation", Journal of Molecular Biology, 2007, 374:865-876.

Dickson et al., "Essential functions of the 32 kDa subunit of yeast replication protein A", Nucleic Acids Research, 2009, 37(7):2313-2326.

Golub et al., "Interaction of human Rad51 recombination protein with single-stranded DNA binding protein, RPA", Nucleic Acids Research, 1998, 26(23):5388-5393.

Gomes et al., "Structural Analysis of Human Replication Protein A", Journal of Biological Chemistry, Mar. 3, 1995, 270(9):4534-4543.

Grudic et al., "Replication protein A prevents accumulation of single-stranded telomeric DNA in cells that use alternative lengthening of telomeres", Nucleic Acids Research, 2007, 35(21):7267-7278.

Haring et al., "Cellular Functions of Human RPA1: Multiple Roles of Domains in Replication, Repair, and Checkpoints", Journal of Biological Chemistry, Jul. 4, 2008, 283(27):19095-19111.

Henricksen et al., "Replication Protein A Mutants Lacking Phosphorylation Sites for p34cdc2 Kinase Support DNA Replication", Journal of Biological Chemistry, Sep. 30, 1994, 269(39):24203-24208.

Henricksen et al., "Recombinant Replication Protein A: Expression, Complex Formation, and Functional Characterization", Journal of Biological Chemistry, Apr. 15, 1994, 269(15):11121-11132.

Henricksen et al., "Phosphorylation of human replication protein A by the DNA-dependent protein kinase is involved in the modulation of DNA replication", Nucleic Acids Research, 1996, 24(15):3107-3112.

Kemp et al., "An Alternative Form of Replication Protein A Expressed in Normal Human Tissues Supports DNA Repair", Journal of Biological Chemistry, Feb. 12, 2010, 285(7):4788-4797.

Kolpashchikov et al., "Polarity of human replication protein A binding to DNA", Nucleic Acids Research, 2001, 29 (2):373-379.

Majka et al., "Replication Protein A directs Loading of the DNA Damage Checkpoint Clamp to 5'-DNA Junctions", Journal of Biological Chemistry, Sep. 22, 2006, 281(38):27855-27861.

Mass et al., "Replication protein A modulates its interface with the primed DNA template during RNA-DNA primer elongation in replicating SV40 chromosomes", Nucleic Acids Research, 2001, 29(18):3892-3899.

Rodrigo et al., "DNA Replication but Not Nucleotide Excision Repair Is Required for UVC-Induced Replication Protein A Phosphorylation in Mammalian Cells", Molecular and Cellular Biology, Apr. 2000, 20(8):2696-2705.

Shag et al., "Replication-mediated DNA damage by camptothecin induces phosphorylation of RPA by DNA-dependent protein kinase and dissociates RPA:DNA-PK complexes", EMBO Journal, 1999, 18(5):1397-1406.

Tang et al., "Replication Protein A Is a Component of a Complex That Binds the Human Metallothionein IIA Gene Transcription Start Site", Journal of Biological Chemistry, Aug. 30, 1996, 271(35):21637-21644.

Vassin et al., "Replication Protein A (RPA) Phosphorylation Prevents RPA Association with Replication Centers", Molecular and Cellular Biology, Mar. 2004, 24(5):1930-1943.

Walther et al., "A novel assay for examining the molecular reactions at the eukaryotic replication fork: activities of replication protein A required during elongation", Nucleic Acids Research, 1999, 27(2):656-664.

* cited by examiner

Figure 9.

```
DBD-D    QHIVPCTISQLLSATLVDEVFRIGNVEISQVTTIVGIIRHAEKAPTNIVYKIDDMTAAPMD  60
DBD-G    QDVVPCNVNQLLSSTVFDPVFKVRGIIVSQVSIVGVIRGAEKASNHICYKIDDMTAKPIE  60
         *.:***..:***:*::.*  **:::.**  :**:****:**  *.: ********* *::

DBD-D    VRQWVDTDDTSSENTVVPPETYVKVAGHLRSFQNKKSLVAFKIMPLEDMNEFTTHILEVI  120
DBD-G    ARQWFGREKVK-QVTPLSVGVYVKVFGILKCPTGTKSLEVLKIHVLEDMNEFTVNILETV  119
         .***. :.:.  :.*  ..* *:**  : :    . :***.: **::*******..:**..:

DBD-D    NAHMVLSKA    129
DBD-G    NAHMMLDKA    128
         ****:*.**
```

Figure 14.

```
DBD-D      QHIVPCTISQLLSATLVDEVFRIGNVEISQVTIVGIIRHAEKAPTNIVYKIDDMTAAPMD   60
DBD-G      QDVVPCNVNQLLSSTVEDPVEKVRGITVSQVSIVGVIRGAEKASNHICYKIDDMTAKPIE   60
           * .:***. ****:*: .* :* **::  . :*** :****.:.:* ********* *::

DBD-D      VRQWVDTDDTSSENTVVPPETYVKVAGHLRSFQNKKSLVAFKIMPLEDMNEFTTHILEVI  120
DBD-G      ARQWEGREKVK-QVTPLSVGVYVKVEGILKCPTGTKSLEVLKIHVLEDMNEFTVHILETV  119
           .***  .  .   .* *  . ***.*.*:. . .:***..:**  ******* :***..

DBD-D      NAHMVLSKA  129
DBD-G      NAHMLIDKA  128
           ****:: ** 
```

SEQUENCE LISTING

<160> NUMBER OF SEQ ID NOS: 23

<210> SEQ ID NO 1
<211> LENGTH: 1560
<212> TYPE: DNA
<213> ORGANISM: Homo sapiens

<400> SEQUENCE: 1

```
tctagtaaaa atgcattttt atagagatgt tgggaaaggc ttcttgaaat tacacgtggg      60
acttttaata gataggcgct ttgaccagct aagcaacagg gctcccctcg tgtgggactt     120
ttagaatgta gcaaccactg acacgcaggg aaggattatg cgatcaggtg agaaggtggc     180
cgaccctgac tggctggaag cagatgcatt ctggtagttg attggtccac aggtagcgtg     240
acgcttgtca cgtcctcagc ctcccagcat tcaatcgtag cctttcggac agctcgaagc     300
ccttctgtgg agagctcgaa gccttctgtg gagaactcaa agccgtccgt ggagcccag      360 acgagccaaa gcccaccttc tcctcagcct gagctgtctt gaagatgagt aagagtgggt     420
ttgggagcta tggcagcatt tctgctgctg atggagcgag tggaggcagt gaccaactgt     480
gtgagagaga tgcaactcct gctattaaga cccaaagacc taaggtccga attcaggacg     540
ttgtaccgtg taacgtgaac cagcttctca gctctactgt gtttgaccct gtgttcaagg     600 ttagggggaat tatagtttcc caggtctcca tcgtgggggt aatcagaggg gcagagaagg    660
cttcaaatca catttgttac aaaattgatg atatgaccgc gaaaccaatc gaggcccgac     720
agtggtttgg tagagagaaa gtcaagcagg tgactccatt gtcagtcgga gtatatgtca     780
aagtgtttgg tatcctcaaa tgtcccacgg gaacaaagag ccttgaggta ttgaaaattc     840
atgtcctaga ggacatgaac gagttcaccg tgcatattct ggaaacggtc aatgcacaca     900
tgatgctgga taaagcccgt cgtgatacca ctgtagaaag tgtgcctgtg tctccatcag    960
```

```
aagtgaatga tgctggggat aacgatgaga gtcaccgcaa tttcatccag gacgaagtgc    1020
tgcgtttgat tcatgagtgt cctcatcagg aagggaagag catccatgag ctccgggctc    1080
agctctgcga ccttagcgtc aaggccatca aggaagcgat tgattatctg accgttgagg    1140
gccacatcta tcccactgtg gatcgggagc attttaagtc tgctgattga ggcagggaaa    1200
acatcctttc attttcgaa gacccttgca tccagctgtg agtaattttg acctgttgac     1260 ttttaggag taggactaaa aaaaaaaatc tcaagtggca ttctttgtca actcgctgct     1320
tttctaactg ctttgaactt ttcggatttt ctgtatttga agctcagaga gagacggtga    1380
tggataaatt gacaactctg taggatttac tagcaagcta atggaaacat gattttcggg    1440
gaagaaaaac tacagaaaat gtagaaattt attatttaat tgtgttggag cttcttttc     1500 caaaagaaaa actagttgca gtcagggagc cagcgaaaag acaaaaaaaa aaaaaaaaa     1560
```

<210> SEQ ID NO 2
<211> LENGTH: 261
<212> TYPE: PRT
<213> ORGANISM: Homo sapiens

<400> SEQUENCE: 2

```
Met Ser Lys Ser Gly Phe Gly Ser Tyr Gly Ser Ile Ser Ala Ala Asp
 1               5                  10                  15

Gly Ala Ser Gly Gly Ser Asp Gln Leu Cys Glu Arg Asp Ala Thr Pro
            20                  25                  30

Ala Ile Lys Thr Gln Arg Pro Lys Val Arg Ile Gln Asp Val Val Pro
        35                  40                  45

Cys Asn Val Asn Gln Leu Leu Ser Ser Thr Val Phe Asp Pro Val Phe
    50                  55                  60

Lys Val Arg Gly Ile Ile Val Ser Gln Val Ser Ile Val Gly Val Ile
65                  70                  75                  80

Arg Gly Ala Glu Lys Ala Ser Asn His Ile Cys Tyr Lys Ile Asp Asp
                85                  90                  95

Met Thr Ala Lys Pro Ile Glu Ala Arg Gln Trp Phe Gly Arg Glu Lys
            100                 105                 110

Val Lys Gln Val Thr Pro Leu Ser Val Gly Val Tyr Val Lys Val Phe
        115                 120                 125

Gly Ile Leu Lys Cys Pro Thr Gly Thr Lys Ser Leu Glu Val Leu Lys
    130                 135                 140

Ile His Val Leu Glu Asp Met Asn Glu Phe Thr Val His Ile Leu Glu
145                 150                 155                 160

Thr Val Asn Ala His Met Met Leu Asp Lys Ala Arg Arg Asp Thr Thr
                165                 170                 175

Val Glu Ser Val Pro Val Ser Pro Ser Glu Val Asn Asp Ala Gly Asp
            180                 185                 190

Asn Asp Glu Ser His Arg Asn Phe Ile Gln Asp Glu Val Leu Arg Leu
        195                 200                 205

Ile His Glu Cys Pro His Gln Glu Gly Lys Ser Ile His Glu Leu Arg
    210                 215                 220

Ala Gln Leu Cys Asp Leu Ser Val Lys Ala Ile Lys Glu Ala Ile Asp
225                 230                 235                 240

Tyr Leu Thr Val Glu Gly His Ile Tyr Pro Thr Val Ser Arg Glu His
                245                 250                 255

Phe Lys Ser Ala Asp
            260
```

```
<210> SEQ ID NO 3
<211> LENGTH: 16
<212> TYPE: PRT
<213> ORGANISM: Homo sapiens

<400> SEQUENCE: 3

Phe Gly Arg Glu Lys Val Lys Gln Val Thr Pro Leu Ser Val Gly Val
1               5                   10                  15

<210> SEQ ID NO 4
<211> LENGTH: 1512
<212> TYPE: DNA
<213> ORGANISM: Homo sapiens

<400> SEQUENCE: 4
cggccgcgtt ctgtggtttt ccgctattcc cccagacccg caccttctcg gcctctttgc      60
ggagaatcgt gaccaagatg tggaacagtg gattcgaaag ctatggcagc tcctcatacg     120
ggggagccgg cggctacacg cagtccccgg ggggctttgg atcgcccgca ccttctcaag     180
ccgaaaagaa atcaagagcc cgagcccagc acattgtgcc ctgtactata tctcagctgc     240
tttctgccac tttggttgat gaagtgttca gaattgggaa tgttgagatt tcacaggtca     300
ctattgtggg gatcatcaga catgcagaga aggctccaac caacattgtt tacaaaatag     360
atgacatgac agctgcaccc atggacgttc gccagtgggt tgacacagat gacaccagca     420
gtgaaaacac tgtggttcct ccagaaacat atgtgaaagt ggcaggccac ctgagatctt     480
ttcagaacaa aaagagcctg gtagccttta agatcatgcc cctggaggat atgaatgagt     540
tcaccacaca tattctggaa gtgatcaatg cacacatggt actaagcaaa gccaacagcc     600
agccctcagc agggagagca cctatcagca atccaggaat gagtgaagca gggaactttg     660
gtgggaatag cttcatgcca gcaaatggcc tcactgtggc ccaaaaccag gtgttgaatt     720
tgattaaggc ttgtccaaga cctgaagggt tgaactttca ggatctcaag aaccagctga     780
aacacatgtc tgtatcctca atcaagcaag ctgtggattt tctgagcaat gaggggcaca     840
tctattctac tgtggatgat gaccatttta atccacaga tgcagaataa ctggatctaa     900
ctgggtacct gagatatttt acagctggac ctagtttcac aatctgttgt ctccagctct     960
gcatatgtct ggccaggggg cttctaggaa gtaggtttca tctatcaaat gtctcctctg    1020
acttcctttt gaaacttact gctcttctgt tttattttgt tttgtttgaa gctcagaggg    1080
agatgggcaa ttgacaggga tgcaatccag ggtgggattt cttgaggaag ttacaaataa    1140
gcttgttaca acatcaagat agatggaatt ggaaggatgc taccaggaga gtacttacat    1200
agtgctcagg agtttctctt cttaaaatgt ttactgctga agatgagca ggaccagggc     1260 gttataggca gagccctagc cagaaacctg ctggcctctg cctgttttca tttcccactt    1320
tggttgtgtg gcattacttt cagaattgca cttttcctgct tgtcatgact ttttgacaca    1380
cttgccatga cgtgtgtttc tgtgaacatg aagttctgcg gtagtgcctc caggggcaga    1440
ggaaaagaag aagtgttact gcattttgta caaaataaat acagtcatat gtttaataaa    1500
acagttctac cg                                                        1512

<210> SEQ ID NO 5
<211> LENGTH: 270
<212> TYPE: PRT
<213> ORGANISM: Homo sapiens

<400> SEQUENCE: 5

Met Trp Asn Ser Gly Phe Glu Ser Tyr Gly Ser Ser Ser Tyr Gly Gly
1               5                   10                  15
```

```
Ala Gly Gly Tyr Thr Gln Ser Pro Gly Gly Phe Gly Ser Pro Ala Pro
            20                  25                  30

Ser Gln Ala Glu Lys Lys Ser Arg Ala Arg Ala Gln His Ile Val Pro
        35                  40                  45

Cys Thr Ile Ser Gln Leu Leu Ser Ala Thr Leu Val Asp Glu Val Phe
    50                  55                  60

Arg Ile Gly Asn Val Glu Ile Ser Gln Val Thr Ile Val Gly Ile Ile
65                  70                  75                  80

Arg His Ala Glu Lys Ala Pro Thr Asn Ile Val Tyr Lys Ile Asp Asp
                85                  90                  95

Met Thr Ala Ala Pro Met Asp Val Arg Gln Trp Val Asp Thr Asp Asp
            100                 105                 110

Thr Ser Ser Glu Asn Thr Val Val Pro Pro Glu Thr Tyr Val Lys Val
        115                 120                 125

Ala Gly His Leu Arg Ser Phe Gln Asn Lys Lys Ser Leu Val Ala Phe
    130                 135                 140

Lys Ile Met Pro Leu Glu Asp Met Asn Glu Phe Thr Thr His Ile Leu
145                 150                 155                 160

Glu Val Ile Asn Ala His Met Val Leu Ser Lys Ala Asn Ser Gln Pro
                165                 170                 175

Ser Ala Gly Arg Ala Pro Ile Ser Asn Pro Gly Met Ser Glu Ala Gly
            180                 185                 190

Asn Phe Gly Gly Asn Ser Phe Met Pro Ala Asn Gly Leu Thr Val Ala
        195                 200                 205

Gln Asn Gln Val Leu Asn Leu Ile Lys Ala Cys Pro Arg Pro Glu Gly
    210                 215                 220

Leu Asn Phe Gln Asp Leu Lys Asn Gln Leu Lys His Met Ser Val Ser
225                 230                 235                 240

Ser Ile Lys Gln Ala Val Asp Phe Leu Ser Asn Glu Gly His Ile Tyr
                245                 250                 255

Ser Thr Val Asp Asp Asp His Phe Lys Ser Thr Asp Ala Glu
            260                 265                 270

<210> SEQ ID NO 6
<211> LENGTH: 17
<212> TYPE: PRT
<213> ORGANISM: Homo sapiens

<400> SEQUENCE: 6

Val Asp Thr Asp Asp Thr Ser Ser Glu Asn Thr Val Val Pro Pro Glu
1               5                   10                  15

Thr

<210> SEQ ID NO 7
<211> LENGTH: 269
<212> TYPE: PRT
<213> ORGANISM: Artificial
<220> FEATURE:
<223> OTHER INFORMATION: Hybrid Human RPA4/RPA32 Polypeptide (RPA2-
      Basic)

<400> SEQUENCE: 7

Met Trp Asn Ser Gly Phe Glu Ser Tyr Gly Ser Ser Tyr Gly Gly
1               5                   10                  15

Ala Gly Gly Tyr Thr Gln Ser Pro Gly Gly Phe Gly Ser Pro Ala Pro
            20                  25                  30

Ser Gln Ala Glu Lys Lys Ser Arg Ala Arg Ala Gln His Ile Val Pro
```

```
                35                  40                  45
Cys Thr Ile Ser Gln Leu Leu Ser Ala Thr Leu Val Asp Glu Val Phe
 50                  55                  60

Arg Ile Gly Asn Val Glu Ile Ser Gln Val Thr Ile Val Gly Ile Ile
 65                  70                  75                  80

Arg His Ala Glu Lys Ala Pro Thr Asn Ile Val Tyr Lys Ile Asp Asp
                 85                  90                  95

Met Thr Ala Ala Pro Met Asp Val Arg Gln Trp Phe Gly Arg Glu Lys
            100                 105                 110

Val Lys Gln Val Thr Pro Leu Ser Val Gly Val Tyr Val Lys Val Ala
            115                 120                 125

Gly His Leu Arg Ser Phe Gln Asn Lys Lys Ser Leu Val Ala Phe Lys
        130                 135                 140

Ile Met Pro Leu Glu Asp Met Asn Glu Phe Thr Thr His Ile Leu Glu
145                 150                 155                 160

Val Ile Asn Ala His Met Val Leu Ser Lys Ala Asn Ser Gln Pro Ser
                165                 170                 175

Ala Gly Arg Ala Pro Ile Ser Asn Pro Gly Met Ser Glu Ala Gly Asn
            180                 185                 190

Phe Gly Gly Asn Ser Phe Met Pro Ala Asn Gly Leu Thr Val Ala Gln
        195                 200                 205

Asn Gln Val Leu Asn Leu Ile Lys Ala Cys Pro Arg Pro Glu Gly Leu
    210                 215                 220

Asn Phe Gln Asp Leu Lys Asn Gln Leu Lys His Met Ser Val Ser Ser
225                 230                 235                 240

Ile Lys Gln Ala Val Asp Phe Leu Ser Asn Glu Gly His Ile Tyr Ser
                245                 250                 255

Thr Val Asp Asp Asp His Phe Lys Ser Thr Asp Ala Glu
            260                 265

<210> SEQ ID NO 8
<211> LENGTH: 270
<212> TYPE: PRT
<213> ORGANISM: Artificial
<220> FEATURE:
<223> OTHER INFORMATION: Human RPA4 Polypeptide V104A, D112K

<400> SEQUENCE: 8

Met Trp Asn Ser Gly Phe Glu Ser Tyr Gly Ser Ser Tyr Gly Gly
 1               5                  10                  15

Ala Gly Gly Tyr Thr Gln Ser Pro Gly Gly Phe Gly Ser Pro Ala Pro
                 20                  25                  30

Ser Gln Ala Glu Lys Lys Ser Arg Ala Arg Ala Gln His Ile Val Pro
             35                  40                  45

Cys Thr Ile Ser Gln Leu Leu Ser Ala Thr Leu Val Asp Glu Val Phe
 50                  55                  60

Arg Ile Gly Asn Val Glu Ile Ser Gln Val Thr Ile Val Gly Ile Ile
 65                  70                  75                  80

Arg His Ala Glu Lys Ala Pro Thr Asn Ile Val Tyr Lys Ile Asp Asp
                 85                  90                  95

Met Thr Ala Ala Pro Met Asp Ala Arg Gln Trp Val Asp Thr Asp Lys
            100                 105                 110

Thr Ser Ser Glu Asn Thr Val Val Pro Pro Glu Thr Tyr Val Lys Val
            115                 120                 125

Ala Gly His Leu Arg Ser Phe Gln Asn Lys Lys Ser Leu Val Ala Phe
        130                 135                 140
```

```
Lys Ile Met Pro Leu Glu Asp Met Asn Glu Phe Thr Thr His Ile Leu
145                 150                 155                 160

Glu Val Ile Asn Ala His Met Val Leu Ser Lys Ala Asn Ser Gln Pro
                165                 170                 175

Ser Ala Gly Arg Ala Pro Ile Ser Asn Pro Gly Met Ser Glu Ala Gly
            180                 185                 190

Asn Phe Gly Gly Asn Ser Phe Met Pro Ala Asn Gly Leu Thr Val Ala
            195                 200                 205

Gln Asn Gln Val Leu Asn Leu Ile Lys Ala Cys Pro Arg Pro Glu Gly
        210                 215                 220

Leu Asn Phe Gln Asp Leu Lys Asn Gln Leu Lys His Met Ser Val Ser
225                 230                 235                 240

Ser Ile Lys Gln Ala Val Asp Phe Leu Ser Asn Glu Gly His Ile Tyr
                245                 250                 255

Ser Thr Val Asp Asp His Phe Lys Ser Thr Asp Ala Glu
            260                 265                 270

<210> SEQ ID NO 9
<211> LENGTH: 270
<212> TYPE: PRT
<213> ORGANISM: Artificial
<220> FEATURE:
<223> OTHER INFORMATION: Human RPA4 Polypeptide G67R, E70I

<400> SEQUENCE: 9

Met Trp Asn Ser Gly Phe Glu Ser Tyr Gly Ser Ser Tyr Gly Gly
1               5                   10                  15

Ala Gly Gly Tyr Thr Gln Ser Pro Gly Gly Phe Gly Ser Pro Ala Pro
            20                  25                  30

Ser Gln Ala Glu Lys Lys Ser Arg Ala Arg Ala Gln His Ile Val Pro
        35                  40                  45

Cys Thr Ile Ser Gln Leu Leu Ser Ala Thr Leu Val Asp Glu Val Phe
50                  55                  60

Arg Ile Arg Asn Val Ile Ile Ser Gln Val Thr Ile Val Gly Ile Ile
65                  70                  75                  80

Arg His Ala Glu Lys Ala Pro Thr Asn Ile Val Tyr Lys Ile Asp Asp
                85                  90                  95

Met Thr Ala Ala Pro Met Asp Val Arg Gln Trp Val Asp Thr Asp Asp
            100                 105                 110

Thr Ser Ser Glu Asn Thr Val Val Pro Pro Glu Thr Tyr Val Lys Val
        115                 120                 125

Ala Gly His Leu Arg Ser Phe Gln Asn Lys Ser Leu Val Ala Phe
130                 135                 140

Lys Ile Met Pro Leu Glu Asp Met Asn Glu Phe Thr Thr His Ile Leu
145                 150                 155                 160

Glu Val Ile Asn Ala His Met Val Leu Ser Lys Ala Asn Ser Gln Pro
                165                 170                 175

Ser Ala Gly Arg Ala Pro Ile Ser Asn Pro Gly Met Ser Glu Ala Gly
            180                 185                 190

Asn Phe Gly Gly Asn Ser Phe Met Pro Ala Asn Gly Leu Thr Val Ala
            195                 200                 205

Gln Asn Gln Val Leu Asn Leu Ile Lys Ala Cys Pro Arg Pro Glu Gly
        210                 215                 220

Leu Asn Phe Gln Asp Leu Lys Asn Gln Leu Lys His Met Ser Val Ser
225                 230                 235                 240
```

-continued

Ser Ile Lys Gln Ala Val Asp Phe Leu Ser Asn Glu Gly His Ile Tyr
            245                 250                 255

Ser Thr Val Asp Asp His Phe Lys Ser Thr Asp Ala Glu
            260                 265                 270

<210> SEQ ID NO 10
<211> LENGTH: 270
<212> TYPE: PRT
<213> ORGANISM: Artificial
<220> FEATURE:
<223> OTHER INFORMATION: Human RPA4 Polypeptide F135P, Q136T

<400> SEQUENCE: 10

Met Trp Asn Ser Gly Phe Glu Ser Tyr Gly Ser Ser Tyr Gly Gly
1               5                   10                  15

Ala Gly Gly Tyr Thr Gln Ser Pro Gly Gly Phe Gly Ser Pro Ala Pro
            20                  25                  30

Ser Gln Ala Glu Lys Lys Ser Arg Ala Arg Ala Gln His Ile Val Pro
        35                  40                  45

Cys Thr Ile Ser Gln Leu Leu Ser Ala Thr Leu Val Asp Glu Val Phe
    50                  55                  60

Arg Ile Gly Asn Val Glu Ile Ser Gln Val Thr Ile Val Gly Ile Ile
65                  70                  75                  80

Arg His Ala Glu Lys Ala Pro Thr Asn Ile Val Tyr Lys Ile Asp Asp
                85                  90                  95

Met Thr Ala Ala Pro Met Asp Val Arg Gln Trp Val Asp Thr Asp Asp
            100                 105                 110

Thr Ser Ser Glu Asn Thr Val Val Pro Pro Glu Thr Tyr Val Lys Val
        115                 120                 125

Ala Gly His Leu Arg Ser Pro Thr Asn Lys Lys Ser Leu Val Ala Phe
    130                 135                 140

Lys Ile Met Pro Leu Glu Asp Met Asn Glu Phe Thr Thr His Ile Leu
145                 150                 155                 160

Glu Val Ile Asn Ala His Met Val Leu Ser Lys Ala Asn Ser Gln Pro
                165                 170                 175

Ser Ala Gly Arg Ala Pro Ile Ser Asn Pro Gly Met Ser Glu Ala Gly
            180                 185                 190

Asn Phe Gly Gly Asn Ser Phe Met Pro Ala Asn Gly Leu Thr Val Ala
        195                 200                 205

Gln Asn Gln Val Leu Asn Leu Ile Lys Ala Cys Pro Arg Pro Glu Gly
    210                 215                 220

Leu Asn Phe Gln Asp Leu Lys Asn Gln Leu Lys His Met Ser Val Ser
225                 230                 235                 240

Ser Ile Lys Gln Ala Val Asp Phe Leu Ser Asn Glu Gly His Ile Tyr
                245                 250                 255

Ser Thr Val Asp Asp His Phe Lys Ser Thr Asp Ala Glu
            260                 265                 270

<210> SEQ ID NO 11
<211> LENGTH: 270
<212> TYPE: PRT
<213> ORGANISM: Artificial
<220> FEATURE:
<223> OTHER INFORMATION: Human RPA4/RPA32 Hybrid Polypeptide (422: aa
      1-44 of RPA4 -> aa 1-44 of RPA32)

<400> SEQUENCE: 11

Met Ser Lys Ser Gly Phe Gly Ser Tyr Gly Ser Ile Ser Ala Ala Asp
1               5                   10                  15

Gly Ala Ser Gly Gly Ser Asp Gln Leu Cys Glu Arg Asp Ala Thr Pro
            20                  25                  30

Ala Ile Lys Thr Gln Arg Pro Lys Val Arg Ile Gln His Ile Val Pro
        35                  40                  45

Cys Thr Ile Ser Gln Leu Leu Ser Ala Thr Leu Val Asp Glu Val Phe
50                  55                  60

Arg Ile Gly Asn Val Glu Ile Ser Gln Val Thr Ile Val Gly Ile Ile
65                  70                  75                  80

Arg His Ala Glu Lys Ala Pro Thr Asn Ile Val Tyr Lys Ile Asp Asp
            85                  90                  95

Met Thr Ala Ala Pro Met Asp Val Arg Gln Trp Val Asp Thr Asp Asp
            100                 105                 110

Thr Ser Ser Glu Asn Thr Val Val Pro Pro Glu Thr Tyr Val Lys Val
            115                 120                 125

Ala Gly His Leu Arg Ser Phe Gln Asn Lys Lys Ser Leu Val Ala Phe
        130                 135                 140

Lys Ile Met Pro Leu Glu Asp Met Asn Glu Phe Thr Thr His Ile Leu
145                 150                 155                 160

Glu Val Ile Asn Ala His Met Val Leu Ser Lys Ala Asn Ser Gln Pro
                165                 170                 175

Ser Ala Gly Arg Ala Pro Ile Ser Asn Pro Gly Met Ser Glu Ala Gly
            180                 185                 190

Asn Phe Gly Gly Asn Ser Phe Met Pro Ala Asn Gly Leu Thr Val Ala
        195                 200                 205

Gln Asn Gln Val Leu Asn Leu Ile Lys Ala Cys Pro Arg Pro Glu Gly
    210                 215                 220

Leu Asn Phe Gln Asp Leu Lys Asn Gln Leu Lys His Met Ser Val Ser
225                 230                 235                 240

Ser Ile Lys Gln Ala Val Asp Phe Leu Ser Asn Glu Gly His Ile Tyr
                245                 250                 255

Ser Thr Val Asp Asp Asp His Phe Lys Ser Thr Asp Ala Glu
            260                 265                 270

<210> SEQ ID NO 12
<211> LENGTH: 269
<212> TYPE: PRT
<213> ORGANISM: Artificial
<220> FEATURE:
<223> OTHER INFORMATION: Human RPA4/RPA32 Hybrid Polypeptide (242: aa
      45-171 of RPA4 -> aa 45-172 of RPA32)

<400> SEQUENCE: 12

Met Trp Asn Ser Gly Phe Glu Ser Tyr Gly Ser Ser Tyr Gly Gly
1               5                   10                  15

Ala Gly Gly Tyr Thr Gln Ser Pro Gly Gly Phe Gly Ser Pro Ala Pro
            20                  25                  30

Ser Gln Ala Glu Lys Lys Ser Arg Ala Arg Ala Gln Asp Val Val Pro
        35                  40                  45

Cys Asn Val Asn Gln Leu Leu Ser Ser Thr Val Phe Asp Pro Val Phe
50                  55                  60

Lys Val Arg Gly Ile Ile Val Ser Gln Val Ser Ile Val Gly Val Ile
65                  70                  75                  80

Arg Gly Ala Glu Lys Ala Ser Asn His Ile Cys Tyr Lys Ile Asp Asp
            85                  90                  95

Met Thr Ala Lys Pro Ile Glu Ala Arg Gln Trp Phe Gly Arg Glu Lys
            100                 105                 110

```
Val Lys Gln Val Thr Pro Leu Ser Val Gly Val Tyr Val Lys Val Phe
            115                 120                 125
Gly Ile Leu Lys Cys Pro Thr Gly Thr Lys Ser Leu Glu Val Leu Lys
            130                 135                 140
Ile His Val Leu Glu Asp Met Asn Glu Phe Thr Val His Ile Leu Glu
145                 150                 155                 160
Thr Val Asn Ala His Met Met Leu Asp Lys Ala Asn Ser Gln Pro Ser
                165                 170                 175
Ala Gly Arg Ala Pro Ile Ser Asn Pro Gly Met Ser Glu Ala Gly Asn
            180                 185                 190
Phe Gly Gly Asn Ser Phe Met Pro Ala Asn Gly Leu Thr Val Ala Gln
            195                 200                 205
Asn Gln Val Leu Asn Leu Ile Lys Ala Cys Pro Arg Pro Glu Gly Leu
            210                 215                 220
Asn Phe Gln Asp Leu Lys Asn Gln Leu Lys His Met Ser Val Ser Ser
225                 230                 235                 240
Ile Lys Gln Ala Val Asp Phe Leu Ser Asn Glu Gly His Ile Tyr Ser
                245                 250                 255
Thr Val Asp Asp Asp His Phe Lys Ser Thr Asp Ala Glu
            260                 265

<210> SEQ ID NO 13
<211> LENGTH: 262
<212> TYPE: PRT
<213> ORGANISM: Artificial
<220> FEATURE:
<223> OTHER INFORMATION: Human RPA4/RPA32 Hybrid Polypeptide (224: aa
      172-261 of RPA4 -> aa 173-270 of RPA32)

<400> SEQUENCE: 13

Met Trp Asn Ser Gly Phe Glu Ser Tyr Gly Ser Ser Tyr Gly Gly
1               5                   10                  15
Ala Gly Gly Tyr Thr Gln Ser Pro Gly Gly Phe Gly Ser Pro Ala Pro
            20                  25                  30
Ser Gln Ala Glu Lys Lys Ser Arg Ala Arg Ala Gln His Ile Val Pro
            35                  40                  45
Cys Thr Ile Ser Gln Leu Leu Ser Ala Thr Leu Val Asp Glu Val Phe
        50                  55                  60
Arg Ile Gly Asn Val Glu Ile Ser Gln Val Thr Ile Val Gly Ile Ile
65                  70                  75                  80
Arg His Ala Glu Lys Ala Pro Thr Asn Ile Val Tyr Lys Ile Asp Asp
                85                  90                  95
Met Thr Ala Ala Pro Met Asp Val Arg Gln Trp Val Asp Thr Asp Asp
            100                 105                 110
Thr Ser Ser Glu Asn Thr Val Val Pro Pro Glu Thr Tyr Val Lys Val
            115                 120                 125
Ala Gly His Leu Arg Ser Phe Gln Asn Lys Lys Ser Leu Val Ala Phe
            130                 135                 140
Lys Ile Met Pro Leu Glu Asp Met Asn Glu Phe Thr Thr His Ile Leu
145                 150                 155                 160
Glu Val Ile Asn Ala His Met Val Leu Ser Lys Ala Arg Arg Asp Thr
                165                 170                 175
Thr Val Glu Ser Val Pro Val Ser Pro Ser Glu Val Asn Asp Ala Gly
            180                 185                 190
Asp Asn Asp Glu Ser His Arg Asn Phe Ile Gln Asp Glu Val Leu Arg
            195                 200                 205
```

```
Leu Ile His Glu Cys Pro His Gln Glu Gly Lys Ser Ile His Glu Leu
    210                 215                 220

Arg Ala Gln Leu Cys Asp Leu Ser Val Lys Ala Ile Lys Glu Ala Ile
225                 230                 235                 240

Asp Tyr Leu Thr Val Glu Gly His Ile Tyr Pro Thr Val Asp Arg Glu
                245                 250                 255

His Phe Lys Ser Ala Asp
            260
```

<210> SEQ ID NO 14
<211> LENGTH: 262
<212> TYPE: PRT
<213> ORGANISM: Artificial
<220> FEATURE:
<223> OTHER INFORMATION: Human RPA4/RPA32 Hybrid Polypeptide (RPA4-acidic)

<400> SEQUENCE: 14

```
Met Ser Lys Ser Gly Phe Gly Ser Tyr Gly Ser Ile Ser Ala Ala Asp
1               5                   10                  15

Gly Ala Ser Gly Gly Ser Asp Gln Leu Cys Glu Arg Asp Ala Thr Pro
                20                  25                  30

Ala Ile Lys Thr Gln Arg Pro Lys Val Arg Ile Gln Asp Val Val Pro
            35                  40                  45

Cys Asn Val Asn Gln Leu Leu Ser Ser Thr Val Phe Asp Pro Val Phe
    50                  55                  60

Lys Val Arg Gly Ile Ile Val Ser Gln Val Ser Ile Val Gly Val Ile
65                  70                  75                  80

Arg Gly Ala Glu Lys Ala Ser Asn His Ile Cys Tyr Lys Ile Asp Asp
                85                  90                  95

Met Thr Ala Lys Pro Ile Glu Ala Arg Gln Trp Val Asp Thr Asp Asp
            100                 105                 110

Thr Ser Ser Glu Asn Thr Val Val Pro Pro Glu Thr Tyr Val Lys Val
    115                 120                 125

Phe Gly Ile Leu Lys Cys Pro Thr Gly Thr Lys Ser Leu Glu Val Leu
    130                 135                 140

Lys Ile His Val Leu Glu Asp Met Asn Glu Phe Thr Val His Ile Leu
145                 150                 155                 160

Glu Thr Val Asn Ala His Met Met Leu Asp Lys Ala Arg Arg Asp Thr
                165                 170                 175

Thr Val Glu Ser Val Pro Val Ser Pro Ser Glu Val Asn Asp Ala Gly
            180                 185                 190

Asp Asn Asp Glu Ser His Arg Asn Phe Ile Gln Asp Glu Val Leu Arg
    195                 200                 205

Leu Ile His Glu Cys Pro His Gln Glu Gly Lys Ser Ile His Glu Leu
    210                 215                 220

Arg Ala Gln Leu Cys Asp Leu Ser Val Lys Ala Ile Lys Glu Ala Ile
225                 230                 235                 240

Asp Tyr Leu Thr Val Glu Gly His Ile Tyr Pro Thr Val Asp Arg Glu
                245                 250                 255

His Phe Lys Ser Ala Asp
            260
```

<210> SEQ ID NO 15
<211> LENGTH: 20
<212> TYPE: DNA
<213> ORGANISM: Artificial

```
<220> FEATURE:
<223> OTHER INFORMATION: Forward Primer for Human GAPDH

<400> SEQUENCE: 15
gcaccaccaa ctgcttagca                                              20

<210> SEQ ID NO 16
<211> LENGTH: 21
<212> TYPE: DNA
<213> ORGANISM: Artificial
<220> FEATURE:
<223> OTHER INFORMATION: Reverse Primer for Human GAPDH

<400> SEQUENCE: 16
gtcttctggg tggcactgat g                                            21

<210> SEQ ID NO 17
<211> LENGTH: 27
<212> TYPE: DNA
<213> ORGANISM: Artificial
<220> FEATURE:
<223> OTHER INFORMATION: Probe Sequence for Human GAPDH

<400> SEQUENCE: 17
tcgtggaagg actcatgacc acagtcc                                      27

<210> SEQ ID NO 18
<211> LENGTH: 23
<212> TYPE: DNA
<213> ORGANISM: Artificial
<220> FEATURE:
<223> OTHER INFORMATION: Forward Primer for Human RPA2

<400> SEQUENCE: 18
ttgtttgaag ctcagaggga gat                                          23

<210> SEQ ID NO 19
<211> LENGTH: 22
<212> TYPE: DNA
<213> ORGANISM: Artificial
<220> FEATURE:
<223> OTHER INFORMATION: Reverse Primer for Human RPA2

<400> SEQUENCE: 19
ggtagcatcc ttccaattcc at                                           22

<210> SEQ ID NO 20
<211> LENGTH: 20
<212> TYPE: DNA
<213> ORGANISM: Artificial
<220> FEATURE:
<223> OTHER INFORMATION: Probe Sequence for Human RPA2

<400> SEQUENCE: 20
cccaccctgg attgcatccc                                              20

<210> SEQ ID NO 21
<211> LENGTH: 22
<212> TYPE: DNA
<213> ORGANISM: Artificial
<220> FEATURE:
<223> OTHER INFORMATION: Forward Primer for Human RPA4

<400> SEQUENCE: 21
ctcatcagga agggaagagc at                                           22
```

```
<210> SEQ ID NO 22
<211> LENGTH: 22
<212> TYPE: DNA
<213> ORGANISM: Artificial
<220> FEATURE:
<223> OTHER INFORMATION: Reverse Primer for Human RPA4

<400> SEQUENCE: 22
gccctcaacg gtcagataat ca                                              22

<210> SEQ ID NO 23
<211> LENGTH: 19
<212> TYPE: DNA
<213> ORGANISM: Artificial
<220> FEATURE:
<223> OTHER INFORMATION: Probe Sequence for Human RPA4

<400> SEQUENCE: 23
gctccgggct cagctctgc                                                  19
```

US 8,282,918 B2

POLYNUCLEOTIDES ENCODING RPA4/RPA32 HYBRID POLYPEPTIDES

CROSS-REFERENCE TO RELATED APPLICATIONS

The present application is a continuation-in-part under 35 U.S.C. §120 of International Application No. PCT/US2008/071421, filed on Jul. 29, 2008, and published in the English language on Feb. 5, 2009, as International Publication No. WO 2009/018250, which application claims the benefit under 35 U.S.C. §119(e) to U.S. Provisional Application No. 60/952,687, filed on Jul. 30, 2007, the contents of which applications are incorporated by reference herein in their entireties.

STATEMENT REGARDING FEDERALLY SPONSORED RESEARCH OR DEVELOPMENT

This invention was made with U.S. Government Support under grant No. RO1-GM044721 awarded by the U.S. National Institutes of Health (NIH). The U.S. government has certain rights in the invention.

BACKGROUND

The field of the invention relates to replication proteins and variants thereof which may be utilized in methods for assessing and modulating cell proliferation. In particular, the field of the invention relates to replication protein A 32 ("RPA32" otherwise referred to as "RPA2"), replication protein 4 ("RPA4"), variants thereof, polynucleotides encoding the polypeptides, and antisense polynucleotides thereof which may be utilized in methods for assessing and modulating cell proliferation.

The human replication protein A (RPA) is a trimeric complex found not only in human cells but also in other mammalian species and lower eukaryotes. RPA is a single-stranded DNA (ssDNA)-binding protein essential for DNA replication, repair, recombination, and monitoring cellular DNA-damage at cell cycle checkpoints. The three peptides of human RPA have molecular masses of approximately 70 kD (for the polypeptide called "RPA70" or alternatively "RPA1"); 32 kD (for the polypeptide called "RPA32" or alternatively "RPA2"); and 14 kD (for the polypeptide called "RPA14" or alternatively "RPA3"). All three polypeptides have been cloned and their encoding sequences have been reported (Erdile et al., 1991, J. BIOL. CHEM. 266:12090-12098; Erdile et al., 1990, J. Biol. Chem. 265:3177-3182; and Umbricht et al., 1993, J. BIOL. CHEM. 268:6131-6138).

RPA has been observed to exhibit functional activities associated with several characterized domains of the three RPA polypeptides. For example, RPA has been observed to bind ssDNA via several identified DNA-binding domains (DBDs) in the three polypeptides. RPA70 contains four domains: an N-terminal DBD-F domain and DNA binding domains (DBDs) A, B, and C. RPA32 contains three domains, including an N-terminal phosphorylation domain, a central DNA-binding domain (DBD-D), and a C-terminal winged-helix domain involved in protein-protein interactions. RPA14 includes a single domain referred to as DBD-E. Not all of the domains referred to as "DBDs" are involved directly in binding ssDNA. The N-terminal DBD-F domain of RPA70 is implicated in protein-protein interactions in DNA metabolism. The DBD-E domain (i.e., RPA14) has been shown to be structurally important for the formation of the RPA trimer.

In addition to RPA70, RPA32, and RPA14, human cells also have a homolog of RPA32, called RPA4. This subunit is expressed in colon mucosal and placental cells, and RPA4 is also detected in three of fourteen human cell lines examined (Keshav et al., "Rpa4, a Homolog of the 34-Kilodalton Subunit of the Replication Protein A Complex," MOLEC. CELL. BIOL., June 1995, p. 3119-3128, Vol. 15, No. 6). RPA4 is able to interact with RPA14 and RPA70 to bind ssDNA.

It now has been shown that RPA4 can substitute for RPA32 with respect to some functions requiring RPA32 in human cells. Exogenous RPA4 expression can change the distribution of cells in S-phase caused by a RPA32 knockdown. Furthermore, RPA4 expression leads to an accumulation of cells in G2/M phase. In addition, a hybrid form of RPA32 containing the non-conserved basic region of RPA4 has properties like those of RPA4 in vivo. Recombinant polypeptides and polynucleotides that encode RPA4 or RPA32 variants, such as the disclosed RPA32 hybrids, may be expressed in cells in order to modulate proliferation. Also, expression of RPA4 has been observed to be reduced in proliferating or cancerous cells in comparison to normal cells.

SUMMARY

Disclosed are replication proteins and variants thereof which may be utilized in methods for assessing and modulating cell proliferation. Also disclosed are polynucleotides encoding the disclosed replication proteins and variants thereof. Also disclosed are methods for making and using the disclosed polypeptides and polynucleotides. In some embodiments, the disclosed methods utilize RPA32 polypeptide, RPA4 polypeptide, variant polypeptides thereof, polynucleotides encoding these polypeptides, or antisense polynucleotides thereof in methods for assessing and modulating cell proliferation. The methods may include regulating RPA32 or RPA4 expression in order to modulate cell proliferation.

In some embodiments, the disclosed polypeptides are wild-type or naturally occurring replication proteins. In other embodiments, the disclosed polypeptides are variant, hybrid, or recombinant forms of polypeptides related to polypeptides of the RPA complex. The disclosed polynucleotides may include an isolated polynucleotide comprising a coding sequence for a RPA32 variant polypeptide (e.g., a recombinant hybrid form of RPA32 polypeptide comprising at least a portion of the coding sequence of the RPA4 polypeptide) or a coding sequence for a RPA4 variant polypeptide (e.g., a recombinant hybrid form of RPA4 polypeptide comprising at least a portion of the coding sequence of the RPA32 polypeptide).

The disclosed polynucleotides and polypeptides may include mutants, variants, or hybrids. In some embodiments, the disclosed polynucleotides may include an isolated polynucleotide comprising a coding sequence for an RPA32 variant polypeptide having amino acid sequence identity to one of SEQ ID NOs:7-14. For example, the isolated polynucleotide may comprise a coding sequence for an RPA32 variant polypeptide having at least about 95%, 96%, 97%, 98%, 99%, or 100% amino acid sequence identity to one of SEQ ID NOs:7-14.

In some embodiments, the disclosed RPA32 variant polypeptides have at least one functional or biological activity associated with RPA32, RPA4, or both. For example, the RPA32 variant polypeptide may bind to at least one of RPA1 and RPA3. The RPA32 variant polypeptide may form a tripartite complex with RPA1 and RPA3. In further embodiments, the RPA32 variant polypeptide or an RPA complex comprising the RPA32 variant polypeptide may bind single stranded nucleic acid (e.g., ssDNA). The RPA32 variant polypeptide or an RPA complex comprising the RPA32 variant polypeptide may modulate the proliferation of a cell in which the RPA32 variant polypeptide is expressed. For example, the RPA32 variant polypeptide or an RPA complex comprising the RPA32 variant polypeptide may modulate the proliferation of human tissues or cell lines such as HeLa cells. In some embodiments, the RPA32 variant polypeptide may dominantly interfere with the functional activity of wild type RPA32 polypeptide. The RPA32 variant polypeptide may exhibit a dominant negative phenotype. For example, the RPA32 variant polypeptide may dominantly inhibit cell proliferation in a cell in which the RPA32 variant polypeptide is expressed (e.g., via transfection of a recombinant polynucleotide that expresses the RPA32 variant polypeptide into the cell).

In some embodiments, the disclosed RPA32 variant polypeptides are hybrid polypeptides comprising at least a portion of the amino acid sequence of RPA4. For example, the RPA32 variant polypeptide may comprise SEQ ID NO:3 (FGREKVKQVTPLSVGV). In some embodiments, the RPA32 variant polypeptide comprises SEQ ID NO:3 (FGREKVKQVTPLSVGV) at a region from about amino acid 108 to about amino acid 123 of the RPA32 variant polypeptide. In other embodiments, an RPA32 variant polypeptide has one or more domains (e.g., a phosphorylation domain, a DNA binding domain, or a winged helix domain of RPA32) replaced with a corresponding domain of RPA4 (e.g., a corresponding phosphorylation domain, a DNA binding domain (DBD), or a winged helix domain of RPA4). For example, an RPA32 variant polypeptide may include a substitution of one domain of RPA32 for a corresponding domain of RPA4 (e.g., DBD-D of RPA32 exchanged for DBD-G of RPA4).

The disclosed RPA32 variant polypeptides and RPA4 variant polypeptides may include one or more amino acid substitutions relative to wild type RPA32 polypeptide or wild type RPA4 polypeptide, respectively. For example, an RPA32 variant polypeptide may include one or more amino acid substitutions within a region from about amino acid 108 to about amino acid 123 of the RPA32 variant polypeptide. The amino acid substitution may replace an amino acid of RPA32 with a corresponding amino acid of RPA4. In some embodiments, the amino acid substitutions replace an acidic amino acid of RPA32 (e.g., D and E) with a basic amino acid (e.g., K, R, or H). The RPA32 variant polypeptide may comprise two or more basic amino acid residues within a region from about amino acid 108 to about amino acid 123 of the polypeptide. In other embodiments, the RPA32 variant polypeptide does not comprise more than one acidic amino acid residue within a region from about amino acid 108 to about amino acid 123 of the polypeptide. The disclosed polynucleotides may encode variant polypeptides comprising a coding sequence for a polypeptide selected from SEQ ID NO:7 ("RPA32-basic"); SEQ ID NO:8 ("V104A, D112K"); SEQ ID NO:9 ("G67R, E70I"); SEQ ID NO:10 ("F135P, Q136T" also referred to herein as "aroD")); SEQ ID NO:11 ("422"); SEQ ID NO:12 ("242"); SEQ ID NO:13 ("224"); and SEQ ID NO:14 ("RPA4-acidic").

The disclosed polynucleotides may be recombinant and may include a promoter sequence operably linked to the disclosed polynucleotides for expressing the polynucleotides and encoded polypeptides in a cell. Also disclosed are isolated cells transformed with the recombinant polynucleotides disclosed herein. Recombinant polynucleotides may include vectors (e.g., gene therapy vectors).

Also disclosed are methods of expressing the disclosed wild type and variant polypeptides in a cell. The methods include culturing a cell under conditions suitable for expression of the polypeptide, where the cell is transfected with a recombinant polynucleotide comprising a promoter sequence operably linked to a polynucleotide that encodes the wild type or variant polypeptide.

Also disclosed are methods of regulating RPA32 or RPA4 expression in order to modulate cell proliferation. For example, the disclosed methods may include antisense or small interfering RNA (RNAi) modulation of RPA 32 or RPA4 expression in order to modulate cell proliferation. For example, in some embodiments cells may be transfected or infected with a vector that expresses antisense RPA32 nucleic acid or antisense RPA4 nucleic acid. In other embodiments, cells may be transfected or infected with a vector that expresses RNAi targeting RPA32 nucleic acid (e.g., RPA32 mRNA) or that expresses RNAi targeting RPA4 nucleic acid (e.g., RPA4 mRNA).

The disclosed polynucleotides and polypeptides may be formulated as a pharmaceutical composition that comprises the polynucleotides or polypeptides together with a pharmaceutical excipient. The pharmaceutical compositions may be administered in a method for modulating cell proliferation (e.g., in a method for inhibiting cell proliferation). In some embodiments, the pharmaceutical compositions comprise a recombinant form of a polynucleotide that encodes RPA32, RPA4, or variants thereof.

The disclosed pharmaceutical compositions may comprise RPA32 polypeptide, RPA4 polypeptide, or variant polypeptides as contemplated herein. The disclosed pharmaceutical compositions may comprise a polynucleotide encoding RPA32, a polynucleotide encoding RPA4 polypeptide, or a polynucleotide encoding a variant polypeptide as contemplated herein. The disclosed pharmaceutical compositions may comprise the afore-mentioned polynucleotides in a vector as contemplated herein. The pharmaceutical compositions may be administered in a method for treating a cell proliferation disorder in a patient in need thereof. Cell proliferation disorders may include hyperplasias and cancers (e.g., cancers of the colon mucosal tissue). The pharmaceutical compositions may be administered in a method for gene therapy, for example, in a method in which a vector expressing RPA32, RPA4, or variants thereof is introduced to a cell, or in a method in which a vector modulating the expression of RPA32 or RPA4 is introduced to a cell (e.g., a vector expressing antisense RPA32 RNA, RNAi targeting RPA32 mRNA, antisense RPA4 RNA, or RNAi targeting RPA4 mRNA).

Also contemplated are diagnostic methods related to detecting the disclosed replication proteins or to detecting polynucleotides encoding the disclosed replication proteins in tissues, cells, or samples thereof, or detecting the absence thereof. The disclosed diagnostic methods may include methods for identifying or characterizing a cell as a proliferating cell or a cancerous cell. In some embodiments, the methods may include: (a) obtaining a tissue sample or a cell sample from a test patient (e.g., from a test patient having or suspecting of having a proliferative cell disorder such as hyperplasia or cancer, including, but limited to cervical cancer, colon cancer, renal cancer, or liver cancer); and (b) detecting RPA4 nucleic acid in the test sample or the absence thereof (or detecting RPA4 polypeptide in the test sample or the absence thereof). Optionally, the method may include detecting a control nucleic acid or a control polypeptide in the test sample. Suitable control nucleic acids or control polypeptides, include, but are not limited to GADPH nucleic acid (or polypeptide) and RPA32 nucleic acid or (polypeptide).

Optionally, the method may include comparing the amount of the detected RPA nucleic acid (or RPA4 polypeptide) to the amount of the detected control nucleic acid (or control polypeptide, respectively). Optionally, the method may include detecting RPA4 nucleic acid or the absence thereof (or detecting RPA polypeptide or the absence thereof) in a tissue sample or a cell sample obtained from a normal patient and comparing the amount of the detected RPA4 nucleic acid (or detected RPA4 polypeptide) in the normal sample to the amount of the detected RPA4 nucleic acid (or detected RPA4 polypeptide) in the test sample. Optionally, the method may include detecting control nucleic acid (or control polypeptide) in a tissue sample or a cell sample obtained from a normal patient and comparing the amount of the detected control nucleic acid (or control polypeptide) in the normal sample to the amount of the detected control nucleic acid (or control polypeptide) in the test sample.

Also contemplated herein are kits for performing the disclosed methods. For example, kits for performing the methods of modulating cell proliferation (e.g., inhibiting cell proliferation) are contemplated as are kits for performing the methods of detecting the disclosed replication proteins (e.g., RPA32, RPA4, and variants thereof), as are kits for performing methods of detecting polynucleotides encoding the disclosed replication proteins (e.g. RPA32, RPA4, and variants thereof). For example, contemplated kits may include: (a) a first oligonucleotide that hybridizes specifically to a polynucleotide encoding RPA4 polypeptide; and (b) a second oligonucleotide that hybridizes specifically to a polynucleotide encoding RPA32 polypeptide. Primers comprising the first oligonucleotide and the second oligonucleotide are contemplated, for example, a first primer pair where at least one of the first primer pair comprises the first oligonucleotide (i.e., the oligonucleotide that hybridizes specifically to the polynucleotide encoding the RPA4 polypeptide), and a second primer pair where at least one of the second primer pair comprises the second oligonucleotide (i.e., the oligonucleotide that hybridizes specifically to the polynucleotide encoding the RPA32 polypeptide). Probes comprising the first oligonucleotide and the second oligonucleotide also are contemplated, for example, a first probe comprising the first oligonucleotide (i.e., the oligonucleotide that hybridizes specifically to the polynucleotide encoding the RPA4 polypeptide), and a second probe comprising the second oligonucleotide (i.e., the oligonucleotide that hybridizes specifically to the polynucleotide encoding the RPA32 polypeptide).

BRIEF DESCRIPTION OF THE DRAWINGS

FIG. 9 provides an alignment of the RPA32 DNA-binding domain D domain (DBD-D) (SEQ ID NO:5 from amino acid 44 to amino acid 172) and the RPA4 DNA-binding domain G (DBD-G) (SEQ ID NO:2 from amino acid 44 to amino acid 171) and the identified non-conserved amino acid pairs for mutagenesis analysis (i.e., V104A,D112K; G67R,E70I; and F135P,Q136T (also referred to herein as "aroD")).

FIG. 14 provides an alignment of DBD-D (SEQ ID NO:5 from amino acid 44 to amino acid 172) and DBD-G (SEQ ID NO:2 from amino acid 44 to amino acid 171). A non-conserved region was identified at RPA32 amino acid positions 108-124 and RPA4 amino acid positions 108-123 (shown as boxed).

FIG. 20(a) illustrates hybrid constructs: XhoI, AflII, SpeI, and KpnI sites flank the domains (designated above the RPA2 schematic); RPA2 domains are black and RPA4 domains are grey; Names of construct represent which PD, DBD, and WHD they contain and are designated to the right of each schematic; DBD-D, RPA2 DBD; DBD-G, RPA4 DBD; Native, natural forms; Hybrid, RPA2 and RPA4 combinations; Core, DBDs only. FIG. 20(b) illustrates the results of RPA2 siRNA knockdown-rescue experiments. FIG. 20(c) illustrates the results of RPA2 siRNA knockdown-rescue experiments in which cells were synchronized using aphidicolin (aphidocolin-blocked) and subsequently were released from the aphidicolin block. Hours after release is designated to the right of the histograms. Black histograms represent RPA2-depleted cells, and grey histograms represent exogenous RPA-containing cells. Construct expressed is designated above each set of histograms. Sc2, yeast RPA2.

DETAILED DESCRIPTION

Figure 1:
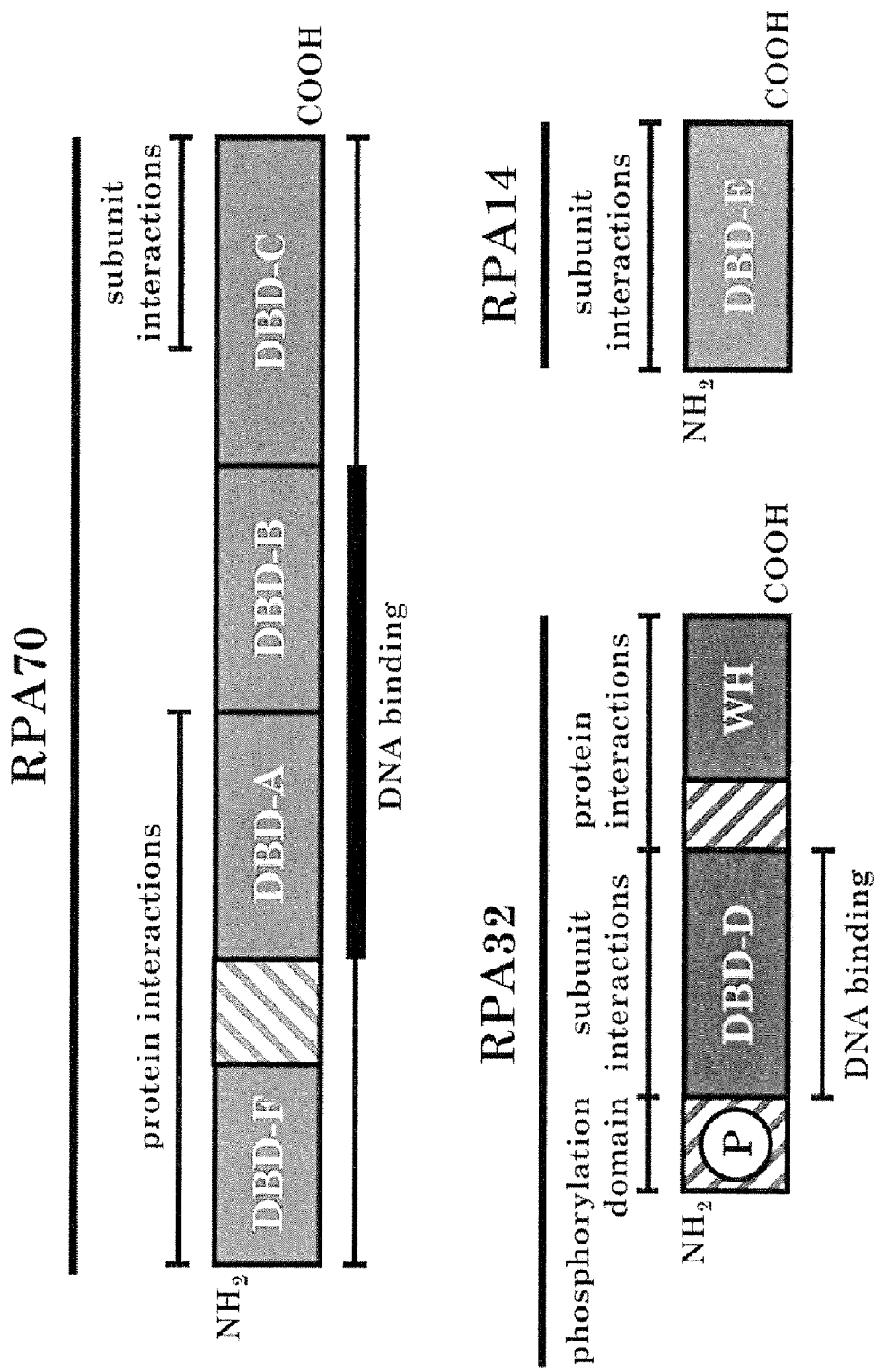
FIG. 1 schematically illustrates the structure of the RPA70 polypeptide (i.e., "RPA1"); the RPA32 polypeptide (i.e., "RPA2"); and the RPA14 polypeptide (i.e., "RPA3").

The present invention is described herein using several definitions, as set forth below and throughout the application.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≦10% of the particular term and "substantially" and "significantly" will mean plus or minus >10% of the particular term.

As used herein, the terms "includes" and "including" shall have the same meaning as the terms "comprises" and "comprising."

As used herein, the phrase "therapeutically effective amount" shall mean that dosage of an active agent that provides the specific pharmacological response for which the active agent is administered in a significant number of patients in need of such treatment. A therapeutically effective amount of an active agent that is administered to a particular patient in a particular instance will not always be effective in treating the conditions/diseases described herein, even though such dosage is deemed to be a therapeutically effective amount by those of skill in the art.

As used herein, a "patient" may be interchangeable with "subject" and means an animal, which may be a human or non-human animal, in need of treatment. Non-human animals may include dogs, cats, horses, cows, pigs, sheep, and the like.

A "patient in need thereof" may include a patient having, suspected of having, or at risk for acquiring a cell proliferative disorder. For example, a patient in need thereof may include a patient having, suspected of having, or at risk for acquiring hyperplasia or cancer, which includes, but is not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, liver cancer (e.g., hepatocellular carcinoma), kidney cancer (e.g., renal cell carcinoma), cervical cancer, Kaposi's sarcoma and ovarian cancer. In some embodiments, the cell proliferative disorder may include a cell proliferative disorder of colon mucosal tissue (e.g., colon cancer).

The term "sample" or "patient sample" is meant to include biological samples such as tissues and bodily fluids. "Bodily fluids" may include, but are not limited to, blood, serum, plasma, saliva, cerebral spinal fluid, pleural fluid, tears, lactal duct fluid, lymph, sputum, and semen. A sample may include nucleic acid, protein, or both.

The term "nucleic acid" or "nucleic acid sequence" refers to an oligonucleotide, nucleotide or polynucleotide, and fragments or portions thereof, which may be single or double stranded, and represents the sense or antisense strand. A nucleic acid may include DNA or RNA, and may be of natural or synthetic origin. For example, a nucleic acid may include mRNA or cDNA. Nucleic acid may include nucleic acid that has been amplified (e.g., using polymerase chain reaction).

An "amino acid sequence" refers to a polymer of amino acids present in a polypeptide or protein.

As used herein, "RPA" is used to designate the replication protein A complex (e.g., the human replication protein A complex). RPA is understood to be a tripartite complex that includes RPA70 (which is a 70 kDa polypeptide interchangeably referred to as "RPA1"); RPA32 (which is a 32 kDa polypeptide interchangeably referred to as "RPA2" and sometimes characterized as a 34 kDa polypeptide); and RPA14 (which is a 14 kDA polypeptide interchangeably referred to as "RPA3" and sometimes characterized as a 13 kDa polypeptide).

"RPA4" is understood to refer to the polypeptide identified in Keshav et al., "Rpa4, a Homolog of the 34-Kilodalton Subunit of the Replication Protein A Complex," MOLEC. CELL. BIOL., June 1995, p. 3119-3128, Vol. 15, No. 6 or the polypeptide encoded by the nucleotide sequence deposited in the National Biotechnology Center Information ("NCBI") database under accession number U24186. RPA4 is a 261 amino acid polypeptide and is understood to include a "phosphorylation domain" at about amino acid residues 1-44; a "DNA-binding domain" at about amino acid residues 45-171; and a "winged-helix domain" at about amino acid residues 172-261. RPA4 is understood to include a non-conserved basic domain in comparison to RPA32 at about amino acid residues 108-123.

"RPA32" (interchangeably referred to herein as "RPA2") is understood to refer to the polypeptide identified in Erdile et al., "The Primary Structure of the 32-kDa Subunit of Human Replication Protein A," J. BIOL. CHEM. Vol. 265, February 25, pp. 3177-3182, 1990, or the polypeptide encoded by the nucleotide sequence deposited in the NCBI database under accession number J05249. RPA32 is a 270 amino acid polypeptide and is understood to include a "phosphorylation domain" at about amino acid residues 1-44; a "DNA-binding domain" at about amino acid residues 45-172; and a "winged-helix domain" at about amino acid residues 173-270. RPA32 is understood to include a non-conserved acidic domain in comparison to RPA4 at about amino acid residues 108-124 (SEQ ID NO:6).

As used herein, a "variant" or "mutant" refers to a polypeptide or a polynucleotide molecule having an amino acid sequence or nucleic acid sequence, respectively, that differs from a reference polypeptide or polynucleotide molecule, respectively. A variant or mutant may have one or more insertions, deletions, or substitutions of an amino acid residue or nucleotide residue relative to a reference molecule. For example, an "RPA32 variant polypeptide" or "RPA32 mutant polypeptide" has one or more insertions, deletions, or substitution of an amino acid residue relative to the RPA32 polypeptide. As used herein, variants or mutant may include "hybrids." An "RPA32/RPA4 hybrid polypeptide" is a RPA32 variant having one or more amino acid substitutions relative to RPA32, wherein the substituted one or more amino acid residues are present in RPA4. An RPA32/RPA4 hybrid polypeptide may include a domain or region of RPA4 exchanged for a domain or region of RPA32. For example, an RPA32/RPA4 hybrid polypeptide may include a basic region of RPA4 from about amino acids 108-123 exchanged for an acidic region of RPA32 from about amino acids 108-124.

As described herein, variants, mutants, or hybrids (e.g., an RPA32 variant or mutant polypeptide) may have 99%, 98%, 97%, 96%, 95%, 94%, 93%, 92%, 91%, 90%, 80%, 70%, 60%, or 50% amino acid sequence identity (or nucleic acid sequence identity) relative to a reference molecule (e.g., relative to the RPA32 polypeptide or an RPA32/RPA4 hybrid polypeptide). "Percentage sequence identity" may be determined by aligning two sequences using the Basic Local Alignment Search Tool available at the NBCI website (i.e., "bl2seq" as described in Tatiana A. Tatusova, Thomas L. Madden (1999), "Blast 2 sequences—a new tool for comparing protein and nucleotide sequences", FEMS Microbiol Lett. 174:247-250)).

The variants, mutants, or hybrids described herein may have one or biological functions exhibited by a reference polypeptide (e.g., RPA4 or RPA32). Variants, mutants, or hybrids may bind to RPA70, RPA14, or both to form a tripartite complex. Variants, mutant, or hybrids may bind to nucleic acid (e.g., ssDNA) either alone or as part of a complex with RPA70, RPA14, or both (e.g., as a tripartite complex). Variants, mutants, or hybrids described herein may exhibit dominant negative phenotypes in view of a reference molecule. Dominant negative mutants may include mutants that dominantly interfere with the activity of RPA32. For example, a dominant negative mutant as disclosed herein may cause a population of cells to accumulate in the G2/M-phase of the cell cycle after the cells have been transfected with a vector that expresses the dominant negative mutant.

The methods disclosed herein may include methods of modulating cell proliferation either in vitro or in vivo (e.g., in a patient in need thereof). As used herein, "modulating" means "changing" or "regulating" and may include "inhibiting" cell proliferation. The methods may include modulating cell proliferation in a cell (e.g. inhibiting cell proliferation in a cell) exhibiting hyperplasia or in a cancerous cell. For example, the methods may include transfecting a cell exhibiting hyperplasia or a cancerous cell with: a recombinant polynucleotide that expresses a replication protein such as RPA32, RPA4, or variants thereof; a recombinant antisense polynucleotide of RNA32 or RPA4; or an RNAi targeting RNA32 mRNA or RNAi targeting RNA4 mRNA.

As used herein, the term "transfection" means the transfer of exogenous nucleic acid into a cell and may include "transducing" and "infecting." Transfection methods may include physical methods and biological methods. Transfection may include transduction (e.g., by infection with a viral vector), electroporation via exposing a cell to an electric current, and gene gun methods. Methods of cell transfection also may include $CaCl_2$, $CaPO_4$, and liposome-mediated transfection. Other methods for introducing DNA into cells may include nuclear microinjection or polycation-, polybrene-, or polyornithine-mediated transfection. Transfection methods may include, but are not limited to, mechanical introduction methods that include introduction of a recombinant polynucleotide (e.g., a plasmid) that expresses a replication protein such as RPA32, RPA4, or variants thereof, and biological methods that include infection or transduction of a cell by a vector (e.g., a viral vector) that expresses a replication protein such as RPA32, RPA4, or variants thereof.

The term "vector" refers to some vehicle by which nucleic acid can be introduced into a host organism or host tissue. The term "vector" may refer to a nucleic acid molecule capable of transporting another nucleic acid to which it has been linked, i.e., a "transgene." There are various types of vectors including plasmid, bacteriophages, cosmids, viruses, and bacteria.

Any of the conventional vectors used for expression in eukaryotic cells may be used for directly introducing nucleic acid into a patient (e.g., expression plasmids and viral expression vectors). Expression vectors containing regulatory elements from eukaryotic viruses may be used in eukaryotic expression vectors (e.g., vectors containing SV40, CMV, or retroviral promoters or enhancers). Exemplary vectors include those that express proteins under the direction of such promoters as the SV40 early promoter, SV40 later promoter, metallothionein promoter, human cytomegalovirus promoter, murine mammary tumor virus promoter, and Rous sarcoma virus promoter. Therapeutic quantities of plasmid nucleic acid can be produced for example, by fermentation in E. coli, followed by purification. Aliquots from the working cell bank are used to inoculate growth medium, and grown to saturation in shaker flasks or a bioreactor according to well known techniques. Plasmid DNA can be purified using standard bioseparation technologies such as solid phase anion-exchange resins. If required, supercoiled DNA can be isolated from the open circular and linear forms using gel electrophoresis or other methods. Purified plasmid DNA can be prepared for injection using a variety of formulations (e.g., lyophilized nucleic acid which may be reconstituted in sterile phosphate-buffered saline (PBS)). The purified nucleic acid may be introduced to a patient by any suitable method (e.g., intramuscular (IM) or intradermal (ID) administration).

As used herein, a "viral vector" (e.g., a retrovirus vector, an adenovirus vector, adeno-associated virus vector, a papilloma virus vector, a Sendai virus vector, a measles virus vector, a pox virus vector, and a yellow fever virus vector) refers to recombinant viral nucleic acid that has been engineered to express a heterologous polypeptide (e.g., a replication protein such as RPA32, RPA4, or variants thereof). The recombinant viral nucleic acid typically includes cis-acting elements for expression of the heterologous polypeptide. The recombinant viral nucleic acid typically is capable of being packaged into a helper virus that is capable of infecting a host cell. For example, the recombinant viral nucleic acid may include cis-acting elements for packaging. Typically, the viral vector is not replication competent or is attenuated. An "attenuated recombinant virus" refers to a virus that has been genetically altered by modem molecular biological methods (e.g., restriction endonuclease and ligase treatment, and rendered less virulent than wild type), typically by deletion of specific genes. For example, the recombinant viral nucleic acid may lack a gene essential for the efficient production or essential for the production of infectious virus.

The polynucleotides and polypeptides disclosed herein may be incorporated in a gene therapy method. The disclosed polynucleotides may be operably linked to a constitutive or inducible promoter to form a gene therapy DNA construct. The promoter may be homologous or heterologous to the endogenous promoter for RPA32 or RPA4 provided that the promoter is active in the cell or tissue type into which the DNA construct will be inserted. Other components of the gene therapy DNA construct may optionally include, as required, DNA molecules designed for site-specific integration (e.g., endogenous flanking sequences useful for homologous recombination), tissue-specific promoter(s), enhancer(s) or silencer(s), DNA molecules capable of providing a selective advantage over the parent cell, DNA molecules useful as labels to identify transformed cells, negative selection systems, cell specific binding agents (such as, for example, for cell targeting), cell-specific internalization factors, and transcription factors to enhance expression by a vector as well as factors to enable vector manufacture.

Means of gene delivery to a cell or tissue in vivo or ex vivo include (but are not limited to) direct injection of bare DNA, ballistic methods, liposome-mediated transfer, receptor-mediated transfer (ligand-DNA complex), electroporation, and calcium phosphate precipitation, as disclosed in, for example, U.S. Pat. No. 4,970,154, WO 96/40958, U.S. Pat. Nos. 5,679,559, 5,676,954, and 5,593,875, the disclosures of which are incorporated by reference herein in their entirety. Means of gene delivery also may include the use of a viral vector such as a retrovirus, adenovirus, adeno-associated virus, pox virus, lentivirus, papilloma virus, herpes simplex virus, yellow fever virus, and use of a DNA-protein conjugate and use of a liposome. The use of gene therapy vectors is described, for example, in U.S. Pat. Nos. 5,672,344, 5,399,346, 5,631,236, and 5,635,399, the disclosures of which are incorporated by reference herein in their entirety.

The polynucleotides and polypeptides disclosed herein may be administered to patients in need thereof in treatment methods or prevention methods. For example, the compounds may be administered as a pharmaceutical composition for modulating cell proliferation in a patient in need thereof.

In some embodiments, the polynucleotides and polypeptides may be formulated as pharmaceutical compositions that include a therapeutically effective amount of the compounds and one or more pharmaceutically acceptable carriers, excipients, or diluents (i.e., agents), which are nontoxic to the cell or mammal being exposed thereto at the dosages and concentrations employed. Often a physiologically acceptable agent is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; or nonionic surfactants such as TWEEN™, polyethylene glycol (PEG), and PLURONICS™.

For in vivo delivery, a gene therapy viral vector may be formulated into pharmaceutical compositions which may be administered by any suitable means, including but not limited to intravenous, subdermal, subcutaneous, and parenteral administration. Pharmaceutical compositions comprising gene therapy viral vectors typically comprise sufficient genetic material to produce a therapeutically effective amount of the protein of interest (i.e., an amount sufficient to reduce or ameliorate symptoms of the disease state in question or an amount sufficient to confer the desired benefit, such as inhibition of cell proliferation). Such pharmaceutical compositions may also contain one or more pharmaceutically acceptable excipients, which include, but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles.

A "therapeutically effective amount" of a gene therapy viral vector may be on the order of from about $10^6$ to $10^{15}$ of the vector (or about $10^8$ to $10^{12}$ of the vector). Dosage treatment may be a single dose schedule or a multiple dose schedule. A patient or subject may be administered one or multiple doses.

The methods contemplated herein also include methods of detecting or assaying for a replication protein in a cell (e.g., RPA32, RPA4, or variants thereof) or a nucleic acid encoding at least a portion of a replication protein in a cell (e.g., a nucleic acid encoding at least a portion of RPA32, RPA4, or variants thereof). The methods thus performed may be utilized to assess whether a patient sample includes proliferating cells or cancerous cells. The methods thus performed may be utilized to identify proliferating cells or cancerous cells in a patient sample. The methods thus performed may be utilized to diagnose hyperplasia or cancer in a patient from whom the sample has been obtained.

As used herein, the terms "detect" and "detecting" may be used interchangeably with the terms "assay" or "assaying," respectively, and include qualitative or quantitative analysis or testing for a polynucleotide or polypeptide in a sample or the absence thereof. Detecting may include, but is not limited to, one or more of: sequencing nucleic acid, amplifying nucleic acid, reverse transcribing nucleic acid, probing nucleic acid, and digesting nucleic acid. As used herein the term "sequencing," as in determining the sequence of a polynucleotide, refers to methods that determine the base identity at multiple base positions or that determine the base identity at a single position. The term "amplification" or "amplifying" refers to the production of additional copies of a nucleic acid sequence. Amplification is generally carried out using polymerase chain reaction (PCR) technologies known in the art.

The present methods and kits for performing the methods may utilize primers, probes, or both. The term "primer" refers to an oligonucleotide that hybridizes to a target nucleic acid and is capable of acting as a point of initiation of synthesis when placed under conditions in which primer extension is initiated (e.g., primer extension associated with an application such as PCR). For example, primers contemplated herein may hybridize to one or more polynucleotide sequences encoding replication proteins (e.g., RPA32, RPA4, and variants thereof). Primers as contemplated herein may comprise one or more polynucleotide sequences of SEQ ID NOs:15, 16, 18, 19, 21, and 22. A "probe" refers to an oligonucleotide that interacts with a target nucleic acid via hybridization. A primer or probe may be fully complementary to a target nucleic acid sequence or partially complementary. The level of complementarity will depend on many factors based, in general, on the function of the primer or probe. For example, probes contemplated herein may hybridize to one or more polynucleotide sequences encoding RPA32, RPA4, or variants thereof. Probes as contemplated herein may comprise one or more polynucleotide sequences of SEQ ID NOs:17, 20, and 23. A primer or probes can be used, for example to detect the presence or absence of polynucleotide sequences encoding RPA32, RPA4, or variants thereof in a sample. Primers and probes can be labeled (e.g., with a fluorophore, a radiolabel, an enzyme, a particulate label, or the like) or unlabeled, or modified in any of a number of ways well known in the art. A primer or probe may specifically hybridize to a target nucleic acid (e.g., hybridize under stringent conditions as discussed herein).

The term "oligonucleotide" is understood to be a molecule that has a sequence of bases on a backbone comprised mainly of identical monomer units at defined intervals. The bases are arranged on the backbone in such a way that they can enter into a bond with a nucleic acid having a sequence of bases that are complementary to the bases of the oligonucleotide. The most common oligonucleotides have a backbone of sugar phosphate units. Oligonucleotides of the method which function as primers or probes are generally at least about 10-15 nucleotides long and more preferably at least about 15 to 25 nucleotides long, although shorter or longer oligonucleotides may be used in the method. The exact size will depend on many factors, which in turn depend on the ultimate function or use of the oligonucleotide. An oligonucleotide (e.g., a probe or a primer) that is specific for a target nucleic acid will "hybridize" to the target nucleic acid under suitable conditions. As used herein, "hybridization" or "hybridizing" refers to the process by which an oligonucleotide single strand anneals with a complementary strand through base pairing under defined hybridization conditions. Oligonucleotides used as primers or probes for specifically amplifying (i.e., amplifying a particular target nucleic acid sequence) or specifically detecting (i.e., detecting a particular target nucleic acid sequence) a target nucleic acid generally are capable of specifically hybridizing to the target nucleic acid.

The present methods may be performed to detect the presence or absence of polynucleotides encoding replication proteins (e.g., RPA32, RPA4, and variants thereof) in a sample. Methods of determining the presence or absence of polynucleotides encoding replication proteins may include a variety of steps known in the art, including one or more of the following steps: reverse transcribing mRNA encoding the replication proteins; amplifying nucleic acid encoding the replication proteins; hybridizing a probe or a primer to nucleic acid encoding the replication proteins (e.g., hybridizing a probe to mRNA, cDNA, or amplified genomic DNA encoding the replication proteins); and sequencing nucleic acid encoding the replication proteins (e.g., sequencing cDNA or amplified DNA encoding the replication proteins).

The present methods also may be performed to detect the presence of absence of replication proteins (e.g., RPA32, RPA4, and variants thereof) in a sample. For example, the disclosed methods may include, but are not limited to, performing immunoassays for detecting the presence or absence of replication proteins in a sample. Immunoassays may include, but are not limited to, ELISA, immunoprecipitation, Western blotting, and the like.

ILLUSTRATIVE EMBODIMENTS

The following embodiments are illustrative and are not intended to limit the scope of the disclosed subject matter.

Embodiment 1. An isolated polynucleotide comprising a coding sequence for a polypeptide of one of SEQ ID NOs:7-14.

Embodiment 2. An isolated polynucleotide comprising a coding sequence for an RPA32 variant polypeptide having at least about 95% amino acid sequence identity to one of SEQ ID NOs:7-14, wherein the polypeptide binds to at least one of RPA1 and RPA3.

Embodiment 3. The isolated polynucleotide of embodiment 1 wherein the polypeptide comprises one of SEQ ID NOs:7-14.

Embodiment 4. The isolated polynucleotide of embodiment 2 or 3, wherein the polypeptide forms a complex with RPA1 and RPA3.

Embodiment 5. The isolated polynucleotide of any of embodiments 2-4, wherein the polypeptide binds single stranded nucleic acid.

Embodiment 6. The isolated polynucleotide of embodiment 6, wherein the nucleic acid is DNA.

Embodiment 7. The isolated polynucleotide of any of embodiments 2-6 wherein the polypeptide inhibits proliferation of eukaryotic cells (e.g., mammalian cells, more specifically human cells, even more specifically HeLa cells).

Embodiment 8. The isolated polynucleotide of any of embodiments 2-7 wherein the polypeptide comprises SEQ ID NO:3 (FGREKVKQVTPLSVGV) or an antisense polynucleotide thereof.

Embodiment 9. The isolated polynucleotide of any of embodiments 2-8 wherein the polypeptide comprises SEQ ID NO:3 (FGREKVKQVTPLSVGV) at a region from about amino acid 108 to about amino acid 123 of the polypeptide.

Embodiment 10. The isolated polynucleotide of any of embodiments 2-9 wherein the polypeptide comprises two or more basic amino acid residues within a region from about amino acid 108 to about amino acid 123 of the polypeptide.

Embodiment 11. The isolated polynucleotide of embodiment 10 wherein the two or more basic amino acid residues are selected from the group consisting of K, R, and H.

Embodiment 12. The isolated polynucleotide of any of embodiments 2-11 wherein the polypeptide does not comprise more than one acidic amino acid residue within a region from about amino acid 108 to about amino acid 123 of the polypeptide.

Embodiment 13. The isolated polynucleotide of embodiment 12 wherein the acidic amino acid residue is selected from the group consisting of D and E.

Embodiment 14. The isolated polynucleotide of any of embodiment 2-13 wherein the polypeptide comprises a phosphorylation domain.

Embodiment 15. The isolated polynucleotide of any of embodiments 2-14 wherein the polypeptide comprises a DNA binding domain.

Embodiment 16. The isolated polynucleotide of any of embodiment 2-15 wherein the polypeptide comprises a winged-helix domain.

Embodiment 17. An isolated polynucleotide comprising a coding sequence for a polypeptide of SEQ ID NO:8 (V104A, D112K).

Embodiment 18. An isolated polynucleotide comprising a coding sequence for a polypeptide of SEQ ID NO:9 (G67R, E70I).

Embodiment 19. An isolated polynucleotide comprising a coding sequence for a polypeptide of SEQ ID NO:10 (F135P, Q136T).

Embodiment 20. A recombinant polynucleotide comprising a promoter sequence operably linked to the polynucleotide of any of embodiments 1-19 or an antisense polynucleotide thereof.

Embodiment 21. An isolated cell transformed with the recombinant polynucleotide of embodiment 20.

Embodiment 22. A gene therapy vector comprising the recombinant polynucleotide of embodiment 20.

Embodiment 23. A method of expressing the polypeptide encoded by the polynucleotide of any of embodiments 1-19, the method comprising culturing a cell under conditions suitable for expression of the polypeptide, wherein said cell is transformed with a recombinant polynucleotide, and said recombinant polynucleotide comprise a promoter sequence operably linked to the polynucleotide of any of embodiments 1-19.

Embodiment 24. A pharmaceutical composition comprising the polynucleotide of any of embodiments 1-19 or an antisense polynucleotide thereof and a pharmaceutically acceptable excipient.

Embodiment 25. A method of modulating cell proliferation comprising transfecting a cell with the recombinant polynucleotide of embodiment 2o.

Embodiment 26. A pharmaceutical composition comprising the recombinant polynucleotide of embodiment 20 or an antisense polynucleotide thereof and a pharmaceutically acceptable excipient.

Embodiment 27. A method of treating a cell proliferation disorder in a patient comprising administering the pharmaceutical composition of embodiment 26.

Embodiment 28. A method of modulating cell proliferation in vivo or in vitro comprising transfecting a cell with a recombinant polynucleotide (e.g., a vector) comprising a promoter sequence operably linked to a polynucleotide comprising a coding sequence for a polypeptide of RPA32 or operably linked to an antisense polynucleotide thereof.

Embodiment 29. A method of modulating cell proliferation in vivo or in vitro comprising transfecting a cell with a recombinant polynucleotide (e.g., a vector) comprising a promoter sequence operably linked to a polynucleotide comprising a coding sequence for a polypeptide of SEQ ID NO:2 (RPA4) or operably linked to an antisense polynucleotide thereof.

Embodiment 30. A method of modulating cell proliferation in vivo or in vitro comprising transfecting a cell with a vector expressing RNAi targeting RNA32 mRNA.

Embodiment 31. A method of modulating cell proliferation in vivo or in vitro comprising transfecting a cell with a vector expressing RNAi targeting RNA4 mRNA.

Embodiment 32. A pharmaceutical composition comprising: (a) a recombinant polynucleotide (e.g., a vector) comprising a promoter sequence operably linked to a polynucleotide comprising a coding sequence for a polypeptide of RPA32 or an antisense polynucleotide thereof; and (b) a pharmaceutically acceptable excipient.

Embodiment 33. A pharmaceutical composition comprising: (a) a recombinant polynucleotide (e.g., a vector) comprising a promoter sequence operably linked to a polynucleotide comprising a coding sequence for a polypeptide of SEQ ID NO:2 (RPA4) or an antisense polynucleotide thereof; and (b) a pharmaceutically acceptable excipient.

Embodiment 34. A pharmaceutical composition comprising: (a) a vector expressing RNAi targeting RNA32 mRNA; and (b) a pharmaceutically acceptable excipient.

Embodiment 35. A pharmaceutical composition comprising: (a) a vector expressing RNAi targeting RNA4 mNA; and (b) a pharmaceutically acceptable excipient.

Embodiment 36. A method of treating a cell proliferation disorder in a patient comprising administering the pharmaceutical composition of any of embodiments 33-36.

Embodiment 37. A method for detecting a proliferating cell or a cancerous cell in a test sample from a patient, the method comprising detecting RPA4 nucleic acid or RPA4 polypeptide in the sample or the absence thereof.

Embodiment 38. The method of embodiment 37, further comprising detecting a control nucleic acid or a control polypeptide in the sample.

Embodiment 39. The method of embodiment 38, wherein the control nucleic acid is RPA32 nucleic acid or the control polypeptide is RPA32 polypeptide.

Embodiment 40. The method of embodiment 38 or 39, further comprising comparing the amount of the detected RPA4 nucleic acid to the amount of the detected control nucleic acid (or comparing the amount of the detected RPA4 polypeptide to the amount of the detected control polypeptide).

Embodiment 41. The method of any of embodiments 37-40, further comprising detecting RPA4 nucleic acid or RPA4 polypeptide in a normal sample from a patient, or the absence thereof, and comparing the amount of the detected RPA4 nucleic acid in the test sample to the amount of the detected RPA4 nucleic acid in the normal sample (or comparing the amount of the detected RPA4 polypeptide in the test sample to the amount of the detected RPA4 polypeptide in the normal sample).

Embodiment 42. The method of embodiment 41, further comprising detecting control nucleic acid or control polypeptide in a normal sample from a patient and comparing the amount of the detected control nucleic acid in the test sample to the amount of the detected control nucleic acid in the normal sample (or comparing the amount of the detected control polypeptide in the test sample to the amount of the detected control polypeptide in the normal sample).

Embodiment 43. The method of any of embodiments 37-43, wherein a lower amount of detected RPA4 nucleic acid or a lower amount of detected RPA4 polypeptide in a test sample as compared to a normal sample indicates that the test sample includes proliferating or cancerous cells.

Embodiment 44. The method of any of embodiments 31-43, comprising detecting RPA4 mRNA in the test sample (or the absence thereof), detecting RPA32 mRNA in the test sample, determining a ratio of the amount of detected RPA4 mRNA in the test sample to the amount of detected RPA32 mRNA in the test sample (i.e., determining the ratio "RPA4 mRNA:RPA32 mRNA" or "RPA4 mRNA/RPA32 mRNA"), comparing the ratio of the test sample to a ratio determined in a normal sample wherein a lower ratio in the test sample as compared to the ratio in the normal sample indicates that the test sample includes proliferating or cancerous cells.

Embodiment 45. The method of embodiment 44, wherein the test sample ratio of RPA4 mRNA to RPA32 mRNA is at least 2×, 3×, 4×, 5×, 10×, 20×, or 50× times lower than the normal sample ratio of RPA4 mRNA to RPA32 mRNA.

Embodiment 46. The method of embodiment 44 or 45, wherein detecting RPA4 mRNA or the absence thereof and detecting RPA32 mRNA comprise performing reverse transcription polymerase chain reaction (rtPCR).

Embodiment 47. The method of any of embodiments 37-46 wherein the test sample is obtained from a patient having, suspected of having, or at risk for developing a cancer selected from cervical cancer, colon cancer, kidney cancer, and liver cancer.

Embodiment 48. The method of any of embodiments 41-47, wherein the normal sample is obtained from a patient known not to have a proliferative disorder or cancer of the cervix, colon, kidney, or liver.

Embodiment 49. A kit for performing any of the methods of embodiments 37-48.

Embodiment 50. A kit comprising: (a) a first oligonucleotide that hybridizes specifically to a polynucleotide encoding RNA4; and (b) a second oligonucleotide that hybridizes specifically to a polynucleotide encoding RNA32.

Embodiment 51. A kit comprising: (a) a first primer pair comprising a first oligonucleotide that hybridizes specifically to a polynucleotide encoding RNA4; and (b) a second primer pair comprising a second oligonucleotide that hybridizes specifically to a polynucleotide encoding RNA32.

Embodiment 52. A kit comprising: (a) a first probe comprising a first oligonucleotide that hybridizes specifically to a polynucleotide encoding RNA4; and (b) a second probe comprising a second oligonucleotide that hybridizes specifically to a polynucleotide encoding RNA32.

EXAMPLES

The following Examples are illustrative and are not intended to limit the disclosed subject matter. Reference is made to the following published manuscripts, the contents of which are incorporated herein by reference in their entireties: Kemp et al., J. Biol. Chem. 2009 Dec. 7 [Epub ahead of print]; Haring et al., Nucleic Acids Res. 2009 Nov. 26 [Epub ahead of print]; Mason et al., J. Biol. Chem. 2009 Feb 20; 284(8): 5324-31 [Epub 2009 Feb. 6]; and '1 Binz et al., Methods Enzymol. 2006; 409:11-38.

Results

I. Polynucleotide and Polypeptide Sequences

SEQ ID NO:1 provides the cDNA sequence for mRNA encoding human RPA4 (GenBank Accession No. U24186 [gi:5729679]. SEQ ID NO:2 is the amino acid sequence for the RPA4 polypeptide. The non-conserved basic domain within the DNA-binding domain G (DBD-G) is underlined FGREKVKQVTPLSVGV (SEQ ID NO:3). SEQ ID NO:4 provides the cDNA sequence for mRNA encoding human RPA32 (GenBank Accession No. J05249) [gi:337349]. SEQ ID NO:5 is the amino acid sequence for the RPA2 polypeptide. The non-conserved acidic domain within the DNA-binding domain D (DBD-D) is VDTDDTSSENTVVPPET (SEQ ID NO:6).

Figure 20:
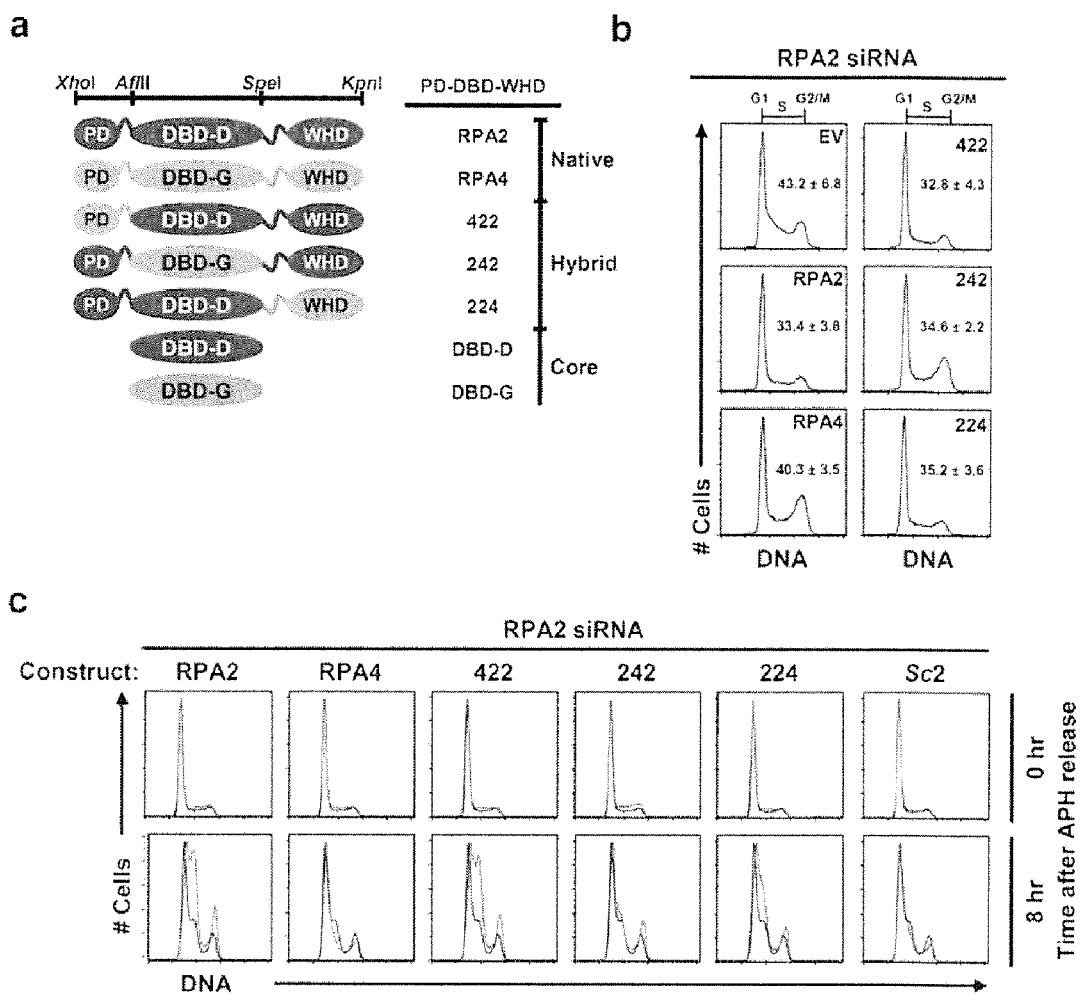
FIG. 20 provides a schematic for hybrid constructs 422, 242, and 224 and illustrates the results of RPA2 knockdown-rescue and aphidocolin-block experiments.

SEQ ID NOS:7-14 provide the amino acid sequence for variant polypeptides. SEQ ID NO:7 is an RPA32 variant polypeptide where the non-conserved acidic domain of RPA32 polypeptide (i.e., amino acids 107-124) has been replaced with the non-conserved basic domain of RPA4 polypeptide (i.e., amino acids 107-123). The replaced domain has the amino acid sequence FGREKVKQVTPLSVGV (SEQ ID NO:3). SEQ ID NO:8 is an RPA32 variant polypeptide where amino acids 104(V) and 112(D) of RPA32 polypeptide are replaced with (A) and (K) amino acids as are present in corresponding positions in RPA4 polypeptide. SEQ ID NO:9 is an RPA32 variant polypeptide where amino acids 67(G) and 70(E) of RPA32 polypeptide are replaced with (R) and (I) amino acids as are present in corresponding positions in RPA4 polypeptide. SEQ ID NO:10 is an RPA32 variant polypeptide where amino acids 135(F) and 136(Q) of RPA32 polypeptide are replaced with (P) and (T) amino acids as are present in corresponding positions in RPA4 polypeptide. SEQ ID NO:11 is an RPA32 variant polypeptide where amino acids 1-44 of RPA32 have been replaced by amino acids 1-44 of RPA4, otherwise referred to as "the 422 hybrid polypeptide." (See FIG. 20.) The 422 hybrid polypeptide includes the phosphorylation domain of RPA4, the DNA binding domain of RPA32, and the winged-helix domain of RPA32. SEQ ID NO:12 is an RPA32 variant polypeptide where amino acids 45-172 of RPA32 have been replaced by amino acids 45-171 of RPA4, otherwise referred to as "the 242 hybrid polypeptide." (See FIG. 20.) The 242 hybrid polypeptide includes the phosphorylation domain of RPA32, the DNA binding domain of RPA4, and the winged-helix domain of RPA32. SEQ ID NO:13 is an RPA32 variant polypeptide where amino acids 173-270 of RPA32 have been replaced by amino acids 172-261 of RPA4, otherwise referred to as "the 224 hybrid polypeptide." (See FIG. 20.) The 224 hybrid polypeptide includes the phosphorylation domain of RPA32, the DNA binding domain of RPA32, and the winged-helix domain of RPA4. SEQ ID NO:14 is an RPA4 variant polypeptide (otherwise called "RPA4-acidic") where amino acids 107-123 of RPA4 have been replaced by amino acids 107-124 of RPA32.

II. Schematic Representations of RPA Complex Polypeptides

Figure 2:
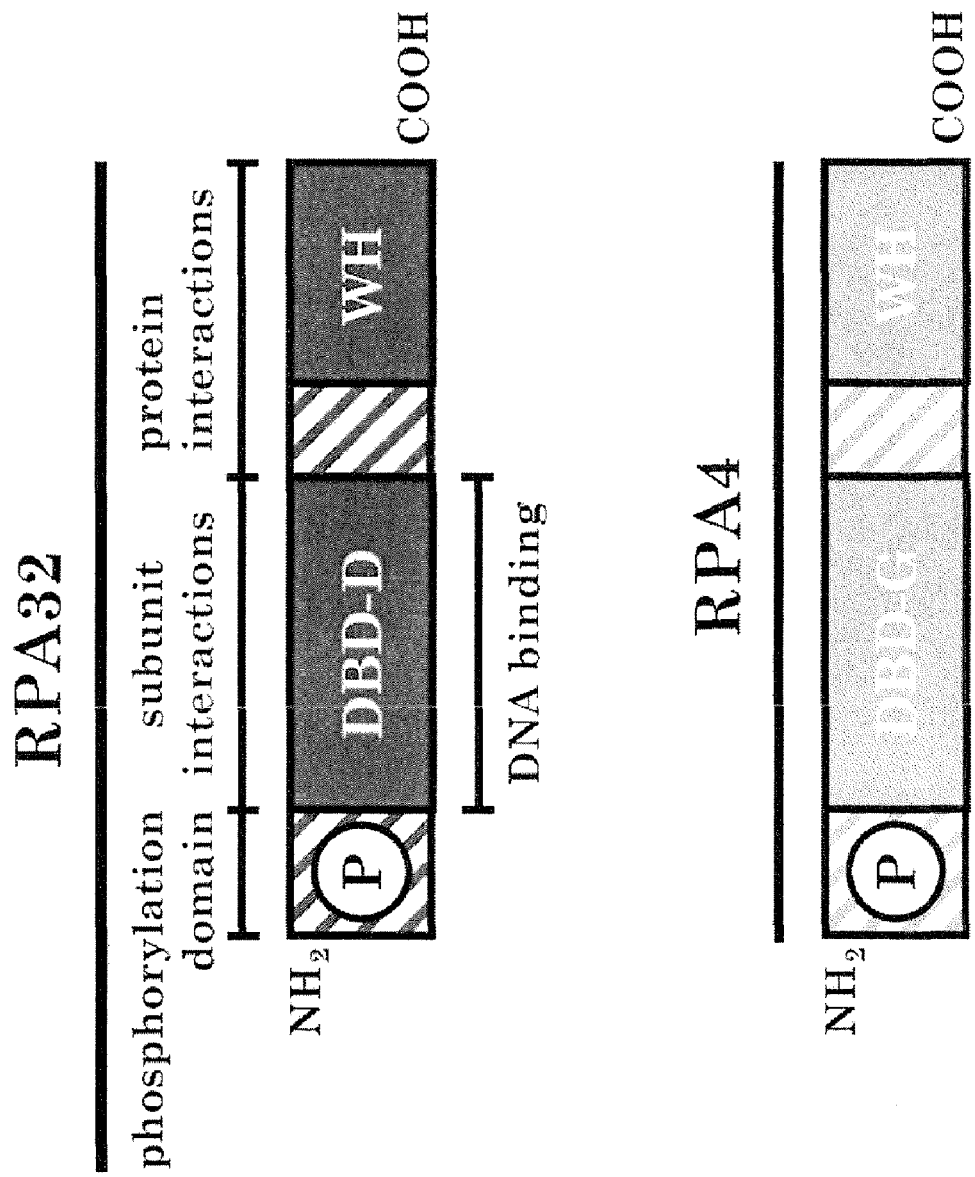
FIG. 2 schematically illustrates the structure of the RPA32 polypeptide (i.e., "RPA2"); and the RPA4 polypeptide.

FIG. 1 provides a schematic representation of the polypeptides that form the replication protein A (RPA) complex: RPA70 (a 70 kD polypeptide also referred to as RPA1); RPA32 (a 32 kD polypeptide also referred to as RPA2 and sometimes characterized as a 34 kD polypeptide); and RPA14 (a 14 kD polypeptide also referred to as RPA3 and sometimes characterized as a 13 kD polypeptide). RPA32 is illustrated as including an N-terminal phosphorylation domain; an internal DNA-binding domain (i.e., DBD-D), which is involved in subunit interactions with the other members of the RPA complex; and a C-terminal winged-helix domain, which is involved in protein interactions. FIG. 2 provides a schematic comparison of RPA32 and RPA4, where RPA4 includes an N-terminal phosphorylation domain; an internal DNA-binding domain (i.e., DBD-G); and a C-terminal winged-helix domain.

III. RPA32 Knockdown and Rescue Experiments

Figure 3:
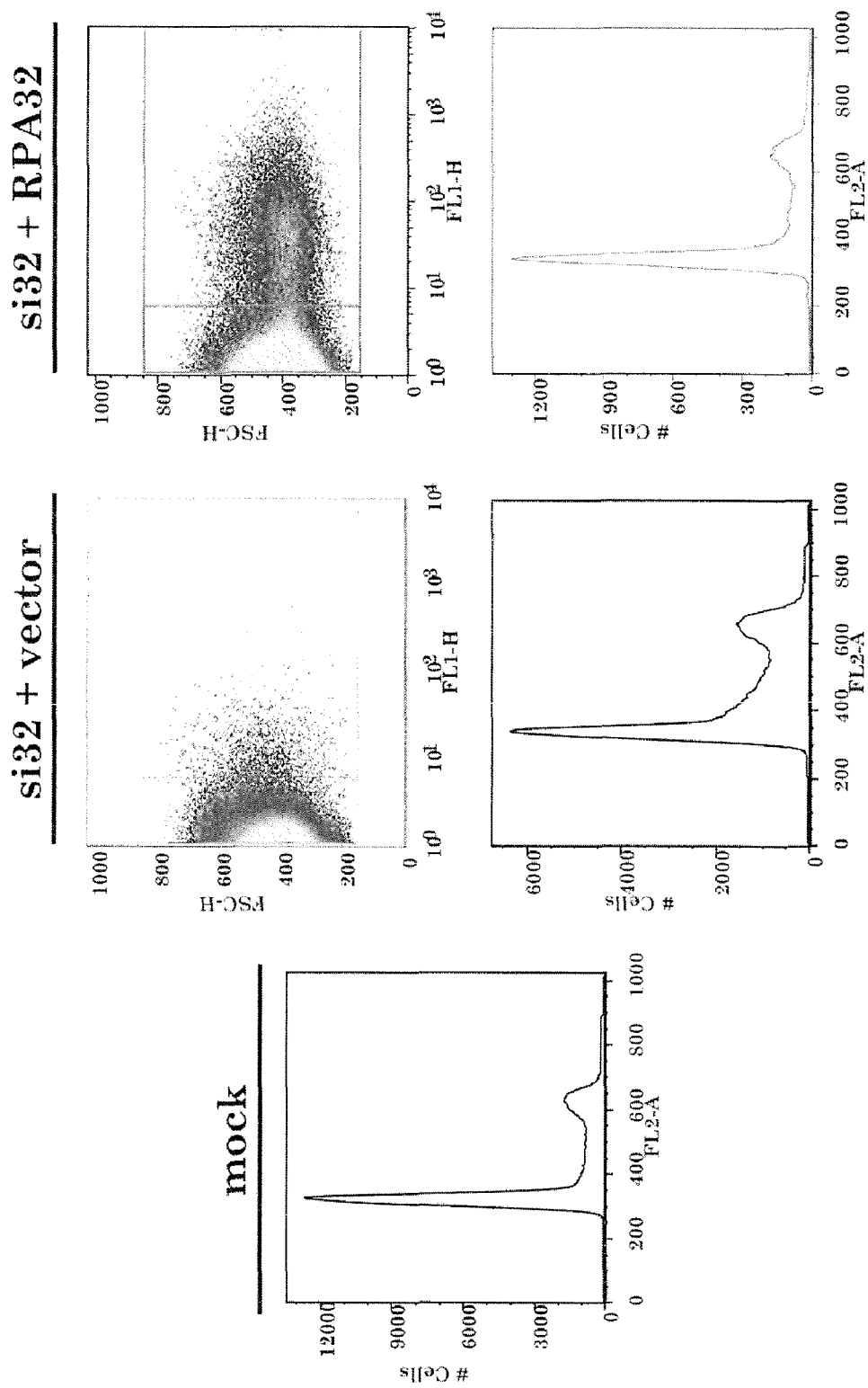
FIG. 3 illustrates cell cycle phenotype after RPA32 knockdown and RPA32 expression. As described in the Examples, HeLa cells were transfected with small interfering RNA ("siRNA") for RPA32 ("si32") and optionally transfected with RPA32 plasmid DNA. The cell cycle phenotype was assessed by flow cytometry.
Figure 4:
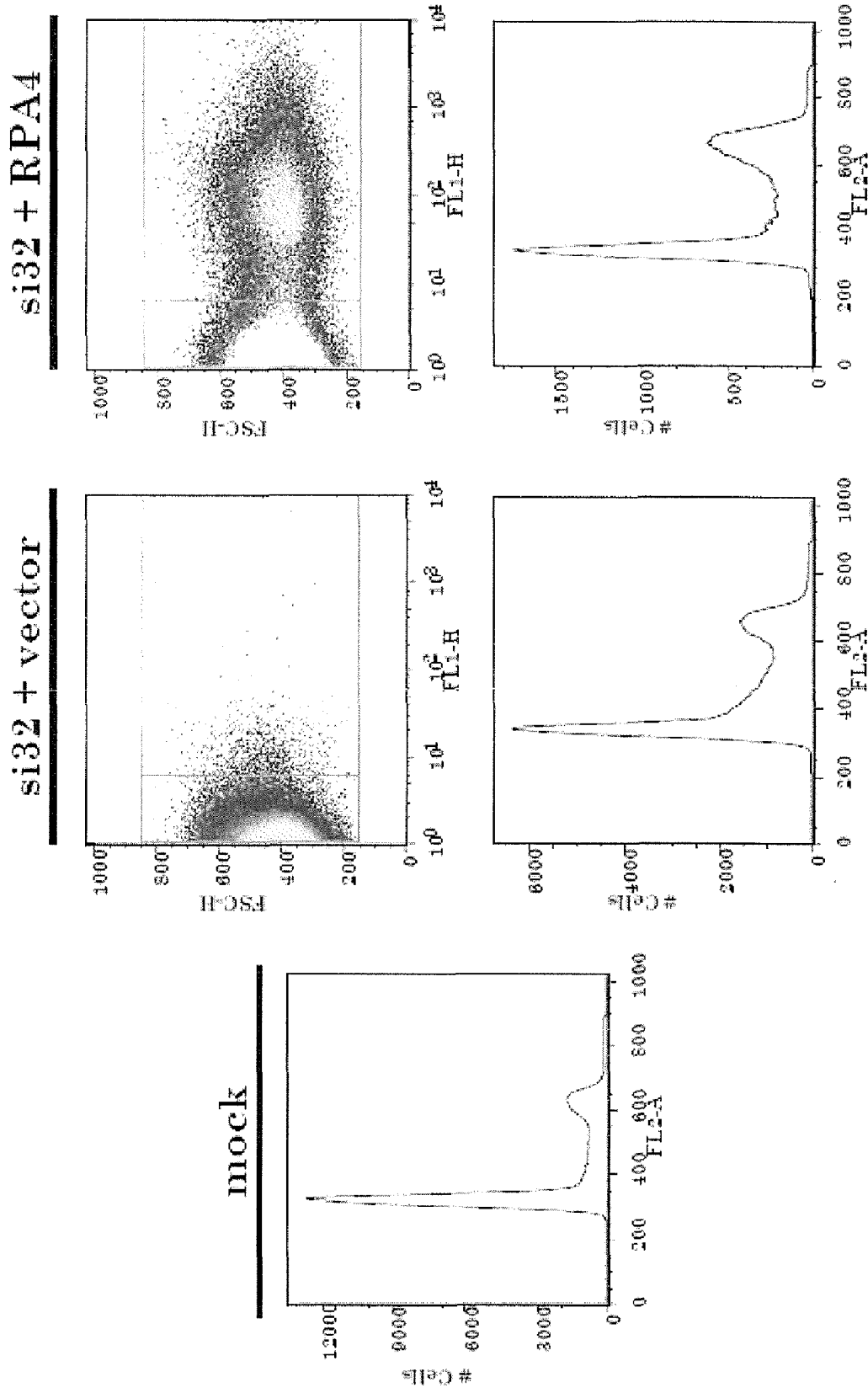
FIG. 4 illustrates cell cycle phenotype after RPA32 knockdown and RPA4 expression. As described in the Examples, HeLa cells were transfected with si32 and optionally transfected with RPA4 plasmid DNA. The cell cycle phenotype was assessed by flow cytometry.
Figure 5:
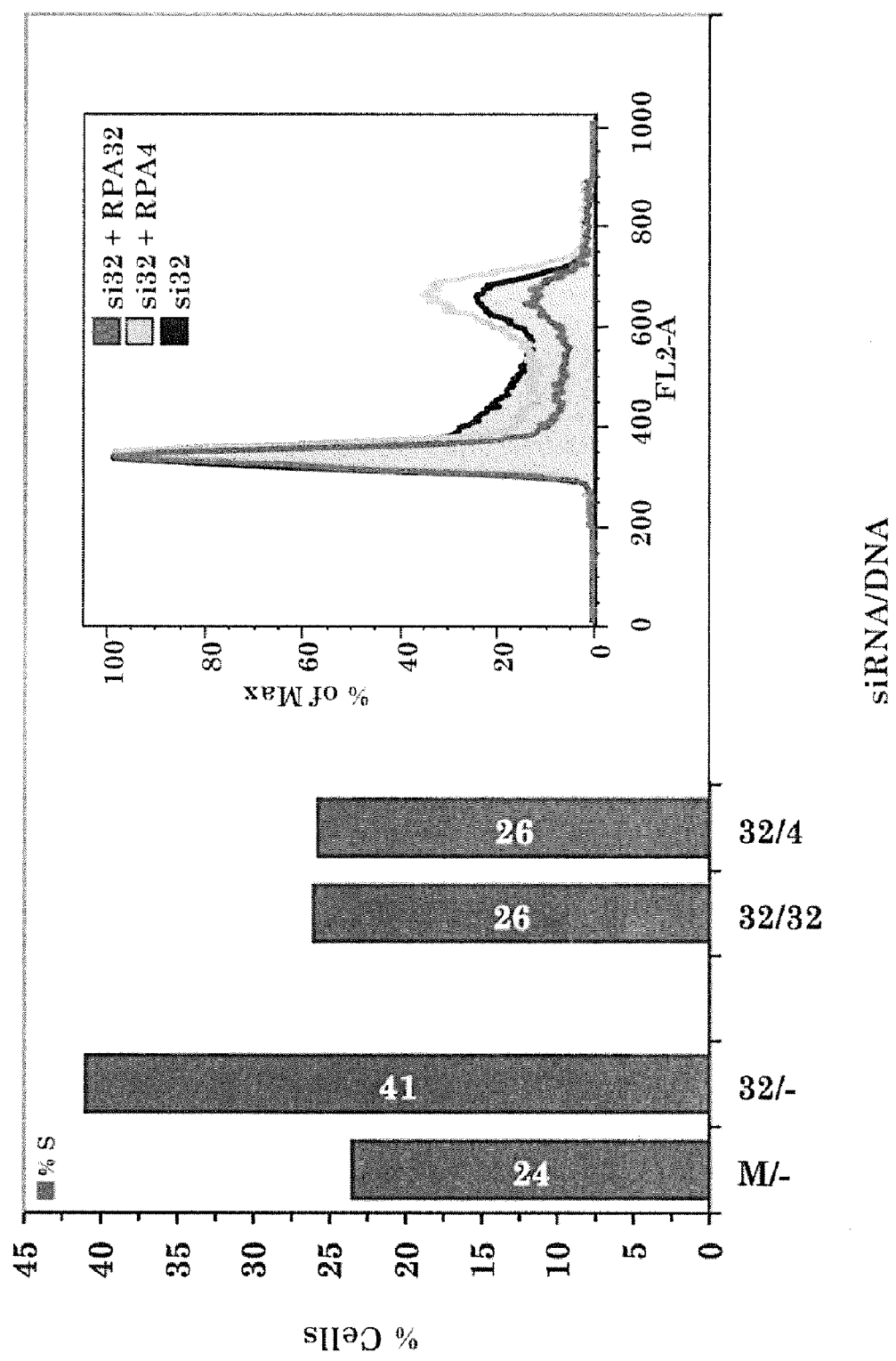
FIG. 5 illustrates the percentage of cells in S-phase after RPA32 knockdown and expression of RPA32 or RPA4. As described in the Examples, HeLa cells were transfected with si32 ("32/", where "M/" designates mock-transfected cells), and optionally transfected with RPA32 plasmid DNA ("/32") or RPA4 plasmid DNA ("/4"), (where "/–" designates non-DNA-transfected cells). The cell cycle phenotype was assessed by flow cytometry.
Figure 6:
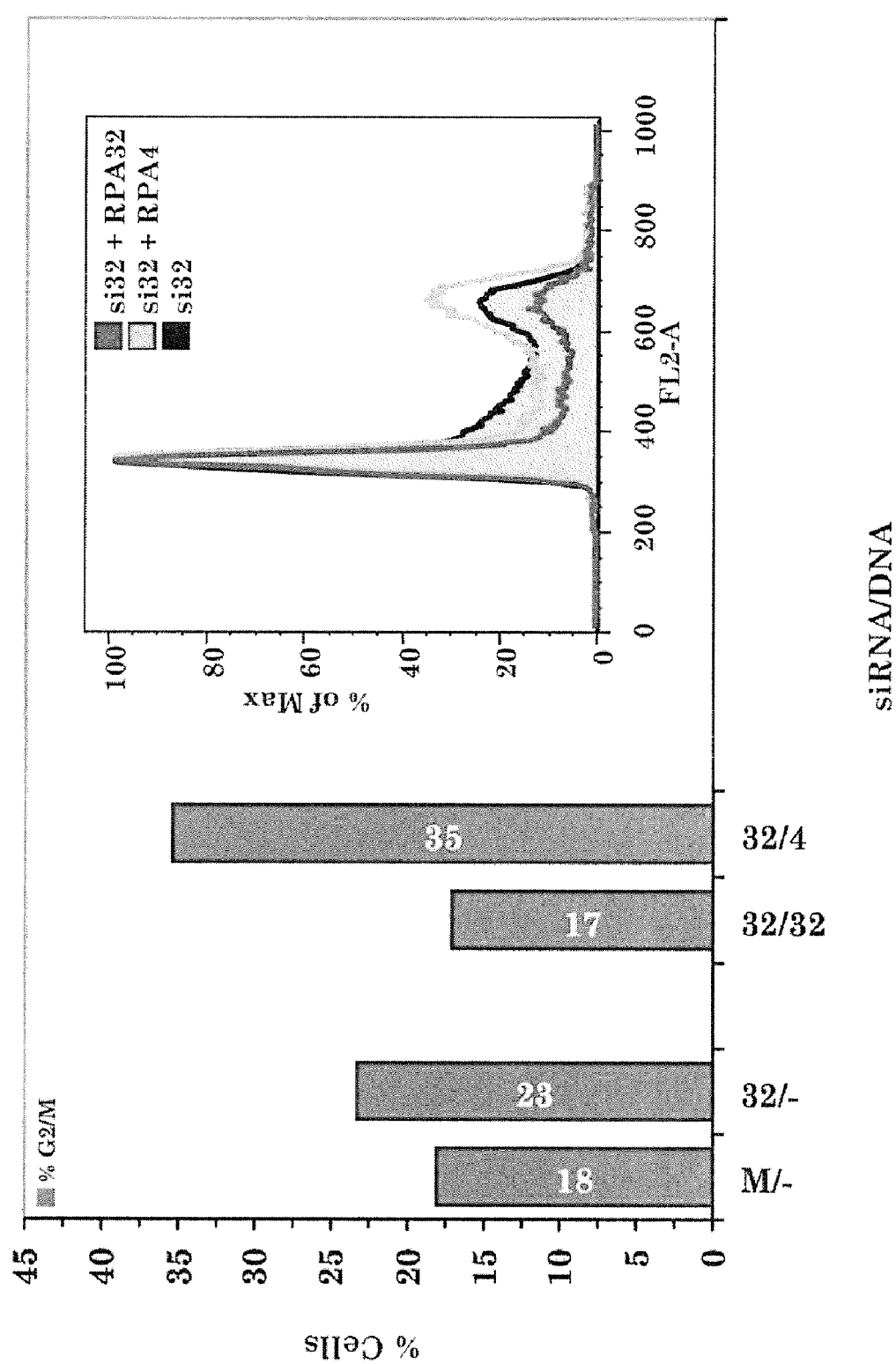
FIG. 6 illustrates the percentage of cells in G2/M-phase after RPA32 knockdown and expression of RPA32 or RPA4. As described in the Examples, HeLa cells were transfected with si32 ("32/", where "M/" designates mock-transfected cells), and optionally transfected with RPA32 plasmid DNA ("/32") or RPA4 plasmid DNA ("/4"), (where "/–" designates non-DNA-transfected cells). The cell cycle phenotype was assessed by flow cytometry.
Figure 7:
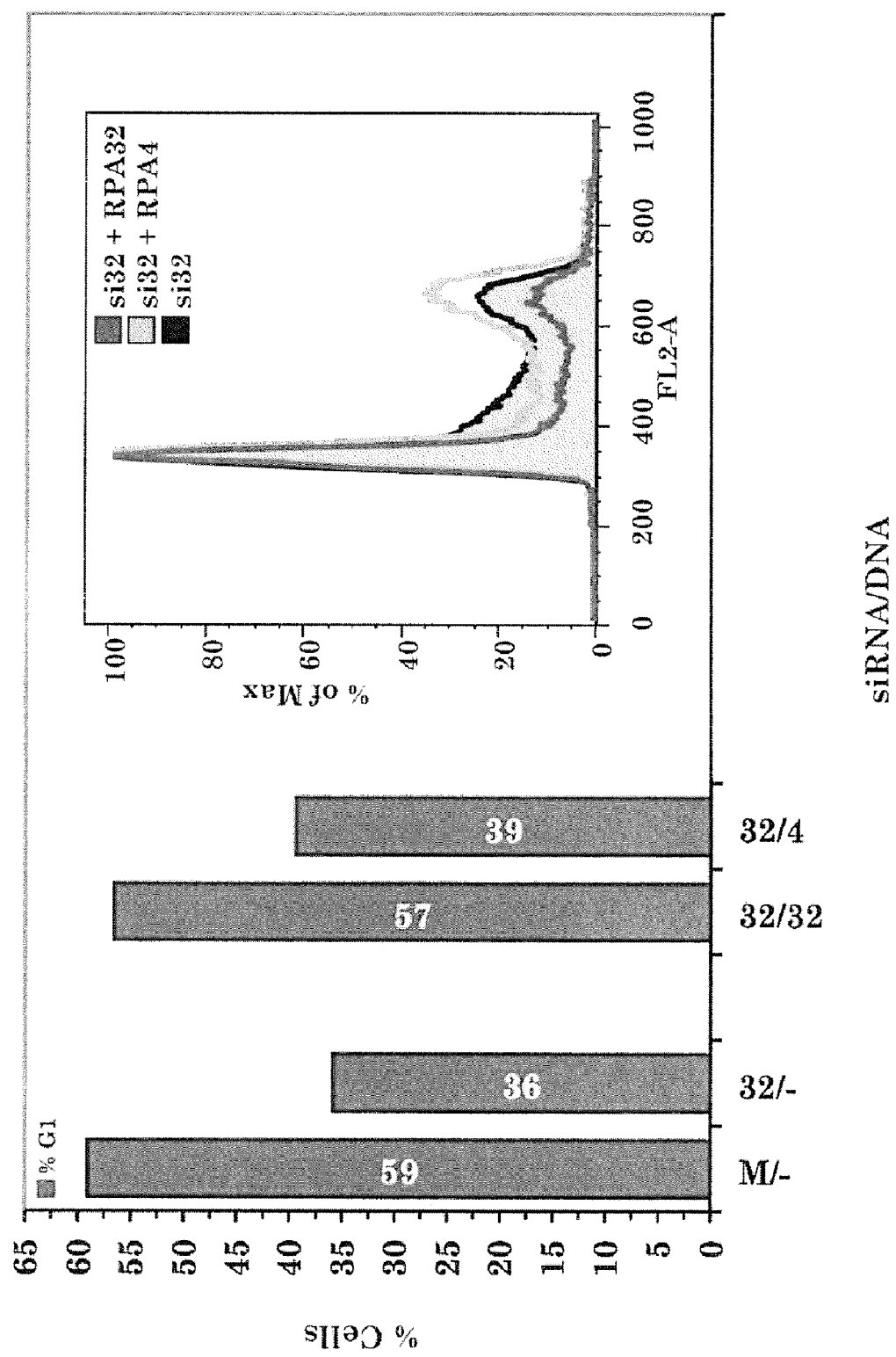
FIG. 7 illustrates the percentage of cells in G1-phase after RPA32 knockdown and expression of RPA32 or RPA4. As described in the Examples, HeLa cells were transfected with si32 ("32/", where "M/" designates mock-transfected cells), and optionally transfected with RPA32 plasmid DNA ("/32") or RPA4 plasmid DNA ("/4"), (where "/–" designates non-DNA-transfected cells). The cell cycle phenotype was assessed by flow cytometry.

HeLa cells were transfected with small inhibitory RNA (siRNA) for RPA32 (i.e., si32) and subsequently were transfected with DNA expression vectors for a GFP-RPA32 fusion polypeptide (where "GFP" is green fluorescent protein) or a GFP-RPA4 fusion polypeptide. The cell phenotype was analyzed by flow cytometry. (See FIGS. 3 and 4.) The results indicate that RPA32 expression or RPA4 expression can ameliorate the effect of si32 knockdown. The percentage of total cells in S-phase (FIG. 5), G2/M-phase (FIG. 6), or G1-phase (FIG. 7) was calculated. The results indicate that RPA4 expression reduces the number of cells in S-phase after RPA32 knockdown. However, RPA4 expression causes an accumulation of cells in G2/M-phase and RPA4 expression cannot restore cells to G1-phase.

IV. Blast Alignment of RPA32 and RPA4 Polypeptides

Figure 8:
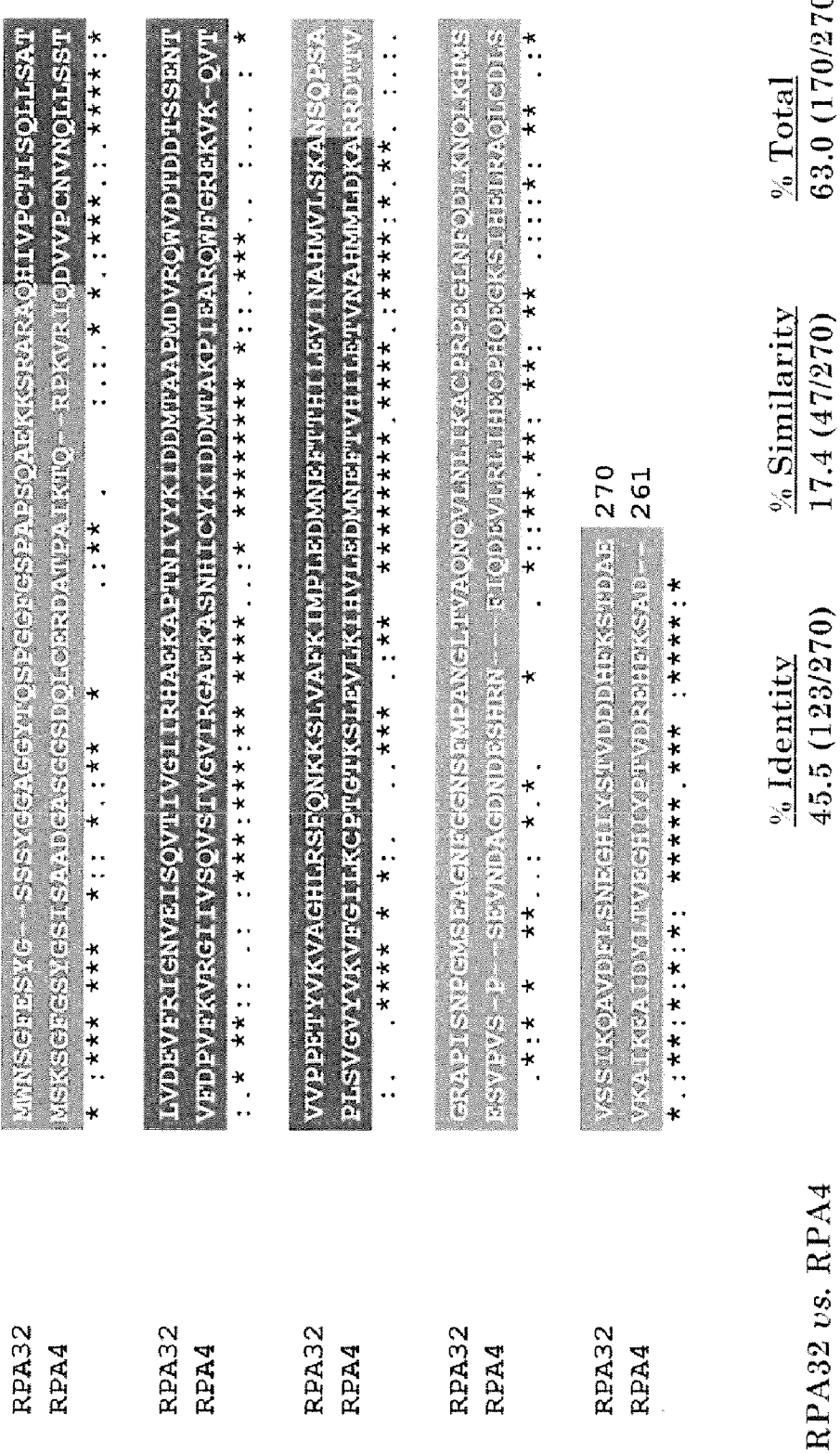
FIG. 8 provides an alignment of RPA32 (SEQ ID NO:5 and RPA4 (SEQ ID NO:2) and illustrates 45.5% sequence identity for RPA4 relative to RPA32 (i.e., 123 identical amino acid residues out of 270 total amino acid residues for RPA32).

RPA32 polypeptide and RPA4 polypeptide were aligned using the Blast algorithm. (See FIG. 8.) The alignment indicates that the RPA32 polypeptide and RPA4 polypeptide have 45.5% amino acid sequence identity (i.e., 123 identical amino acids in RPA4 relative to the 270 total amino acids in RPA32). RPA32 and RPA4 exhibit 36.4% amino acid sequence identity (16/44 amino acids) comparing their respective phosphorylation domains (i.e., amino acids 1-44); RPA32 and RPA4 exhibit 51.9% amino acid sequence identity (67/129 amino acids) comparing their respective DNA-binding domains (i.e., amino acids 45-172 and 45-171, respectively); and RPA32 and RPA4 exhibit 47.8% amino acid sequence identity (33/69 amino acids) comparing their respective winged-helix domains (i.e., amino acids 173-270 and 172-261, respectively). FIG. 9 is an alignment of the RPA32 DBD-D domain and the RPA4 DBD-G domain. Non-conserved residue positions were identified at RPA32 amino acid positions 67, 70, 104, 112, 135, and 136. A schematic model for DBD-D indicating the location of the identified non-conserved amino acids was prepared (data not shown). The model indicated that the non-conserved amino acids are located at external loop positions.

V. RPA32 Variant Polypeptides Having Point Mutations

RPA32 variant polypeptides having point mutations resulting in amino acid substitutions were created, including G67R, E70I ["RPA32-GE"](where the glycine at amino acid position 67 is replaced with arginine and the glutamic acid at amino acid position 70 is replaced with isoleucine); V104A, D112K ["RPA32-VD"] (where the valine at amino acid position 104 is replaced with alanine and the aspartic acid at amino acid position 112 is replaced with lysine); and F135P, Q136T ["RPA32-FQ" also referred to herein as "aroD"] (where the phenylalanine at amino acid position 135 is replaced with proline and the asparagine at amino acid position 136 is replaced with threonine).

Figure 10:
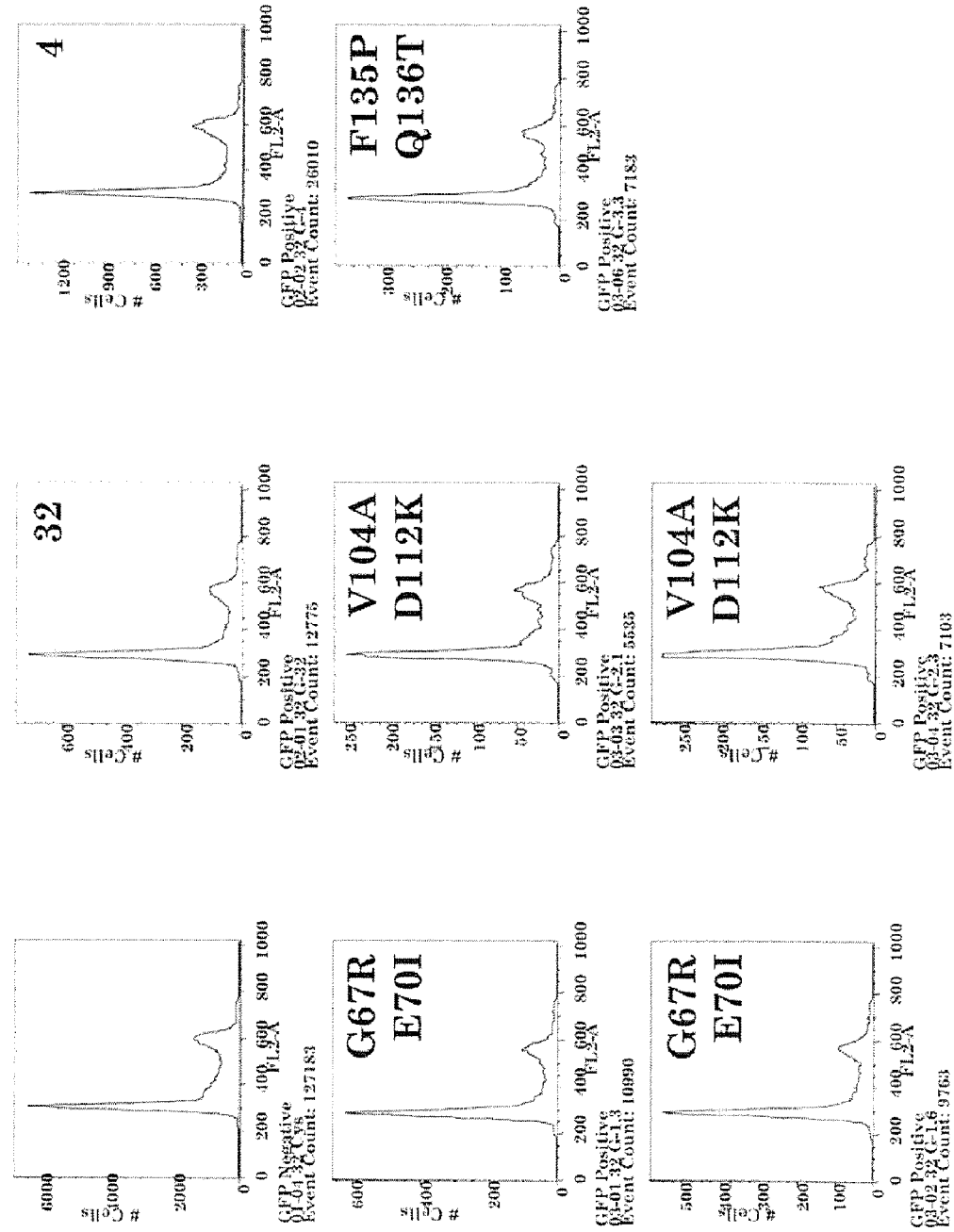
FIG. 10 illustrates the results of cell cycle phenotype analyses of RPA32 (32), RPA4 (4), and point mutants (i.e., VD (SEQ ID NO:8); GE (SEQ ID NO:9); and FQ (SEQ ID NO:10) (also referred to herein as "aroD")). Analyses were performed as described in the Examples.
Figure 11:
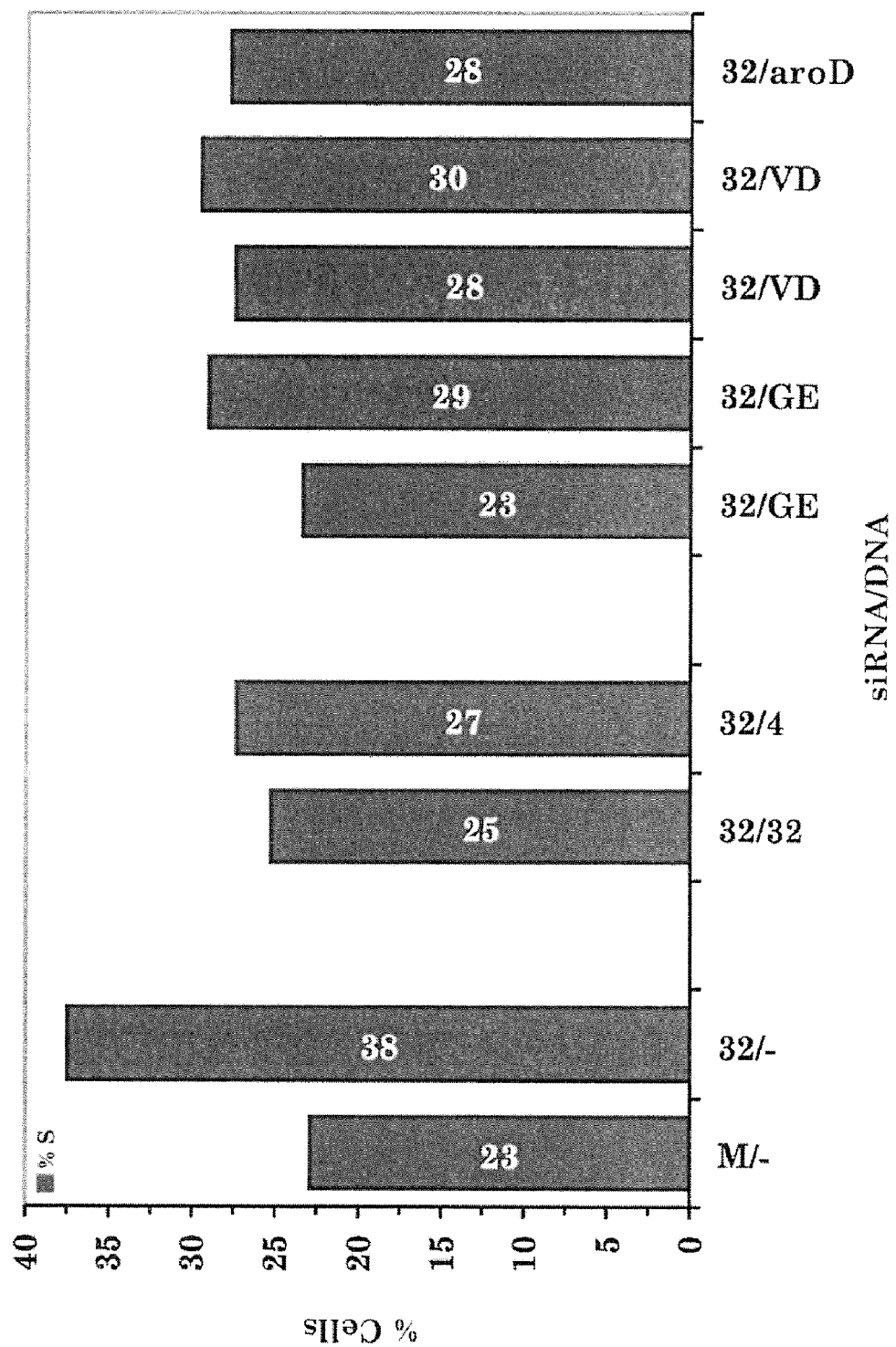
FIG. 11 illustrates the percentage of cells in S-phase after RPA32 knockdown and expression of RPA32 point mutants GE, VD, or aroD (i.e., the "FQ" point mutant). As described in the Examples, HeLa cells were transfected with si32 ("32/", where "M/" designates mock-transfected cells), and optionally transfected with RPA32 plasmid DNA ("/32"), RPA4 plasmid DNA ("/4"), or RPA32 point mutant plasmid DNA ("/GE", "/VD", or "/aroD") (where "/–" designates non-DNA-transfected cells). The cell cycle phenotype was assessed by flow cytometry.
Figure 12:
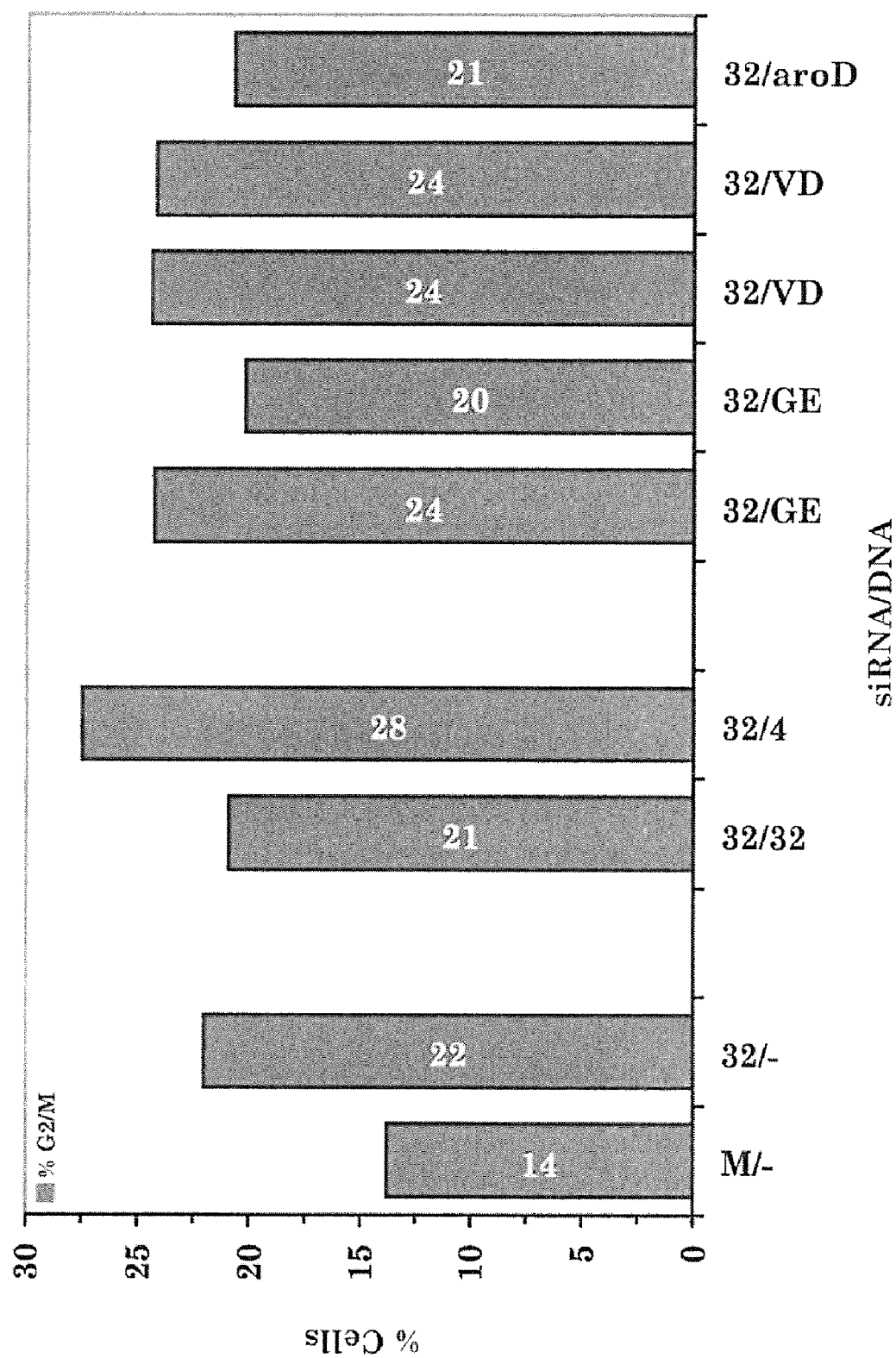
FIG. 12 illustrates the percentage of cells in G2/M-phase after RPA32 knockdown and expression of RPA32 point mutants GE, VD, or aroD. As described in the Examples, HeLa cells were transfected with si32 ("32/", where "M/" designates mock-transfected cells), and optionally transfected with RPA32 plasmid DNA ("/32"), RPA4 plasmid DNA ("/4"), or RPA32 point mutant plasmid DNA ("/GE", "/VD", or "/aroD") (where "/–" designates non-DNA-transfected cells). The cell cycle phenotype was assessed by flow cytometry.
Figure 13:
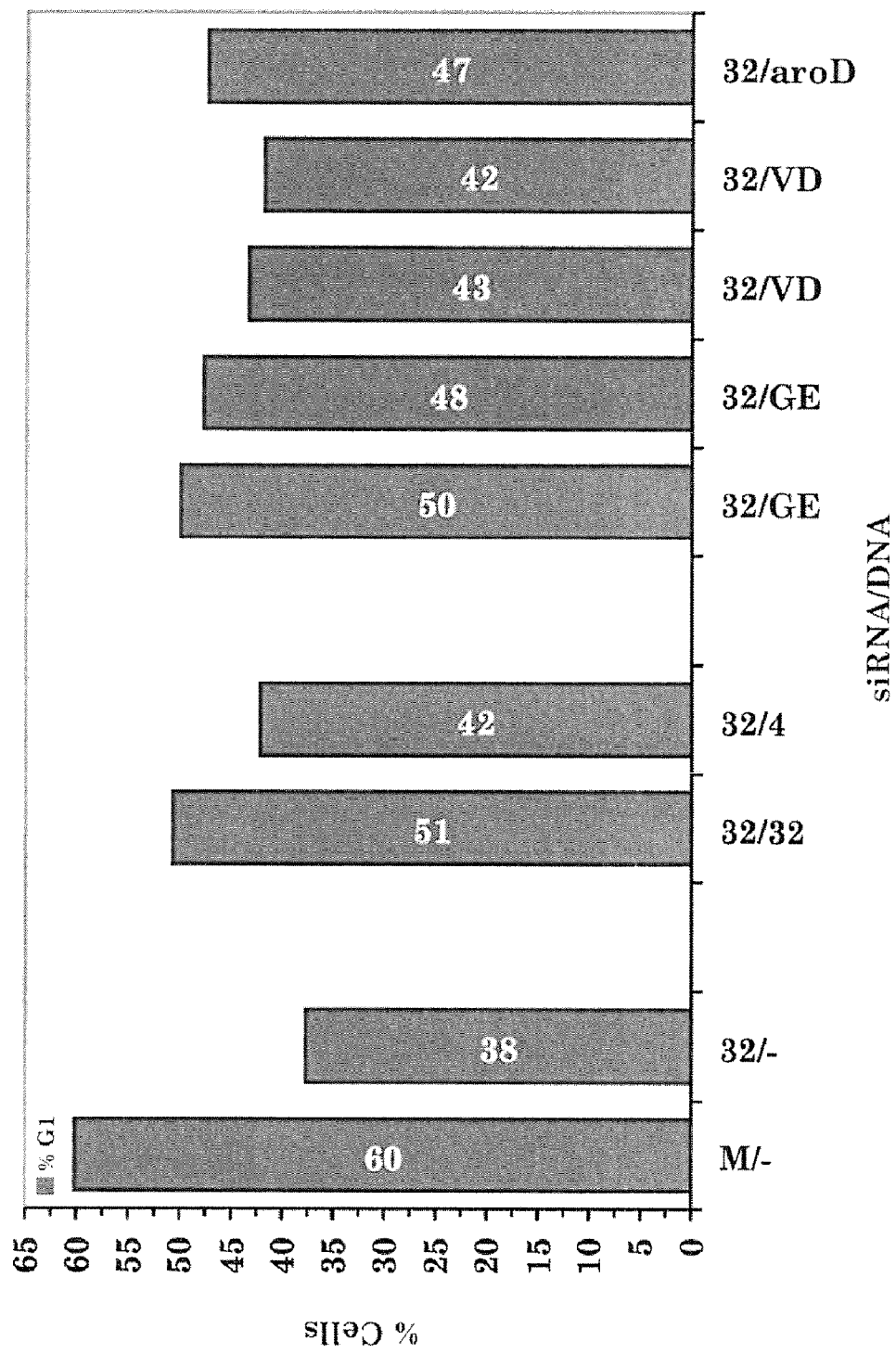
FIG. 13 illustrates the percentage of cells in G1-phase after RPA32 knockdown and expression of RPA32 point mutants GE, VD, or aroD. As described in the Examples, HeLa cells were transfected with siRNA for RPA32 ("32/", where"M/" designates mock-transfected cells), and optionally transfected with RPA32 plasmid DNA ("/32"), RPA4 plasmid DNA ("/4"), or RPA32 point mutant plasmid DNA ("/GE", "/VD", or "/aroD") (where "/−" designates non-DNA-transfected cells). The cell cycle phenotype was assessed by flow cytometry.

HeLa cells were transfected with small inhibitory RNA (siRNA) for RPA32 (i.e., si32) and subsequently transfected with DNA expression vectors for the RPA32 point mutants (expressed as GFP fusion proteins). (See FIG. 10.) The results indicate that the RPA32-VD mutant exhibits an asymmetric shape in its flow cytometry profile which may be characterized as an "S-phase hook." The percentage of total cells in S-phase (FIG. 11), G2/M-phase (FIG. 12), or G1-phase (FIG. 13) was calculated. The results indicate that the RPA32 point mutants can ameliorate the effects of RPA32 knockdown. The results also indicate that expression of the RPA32-VD mutant may cause a slight accumulation of the cells in G2/M-phase and may not restore the cells to G1-phase.

VI. RPA32-Basic Mutant

An alignment of RPA32 DBD-D and RPA4 DBD-G identifies a non-conserved region at RPA32 amino acid positions 108-124 and RPA4 amino acid positions 108-123. (See FIG. 14, boxed sequence). In the non-conserved region of DBD-D, 5 out of the 17 total amino acids are acidic amino acids (D or E). The non-conserved region of DBD-D does not include any basic amino acids (K, R, or H). In the non-conserved region of DBD-G, 3 out of the 16 total amino acids are basic. The non-conserved region of DBD-G also includes a single acidic amino acid (E) at amino acid position 111.

Figure 15:
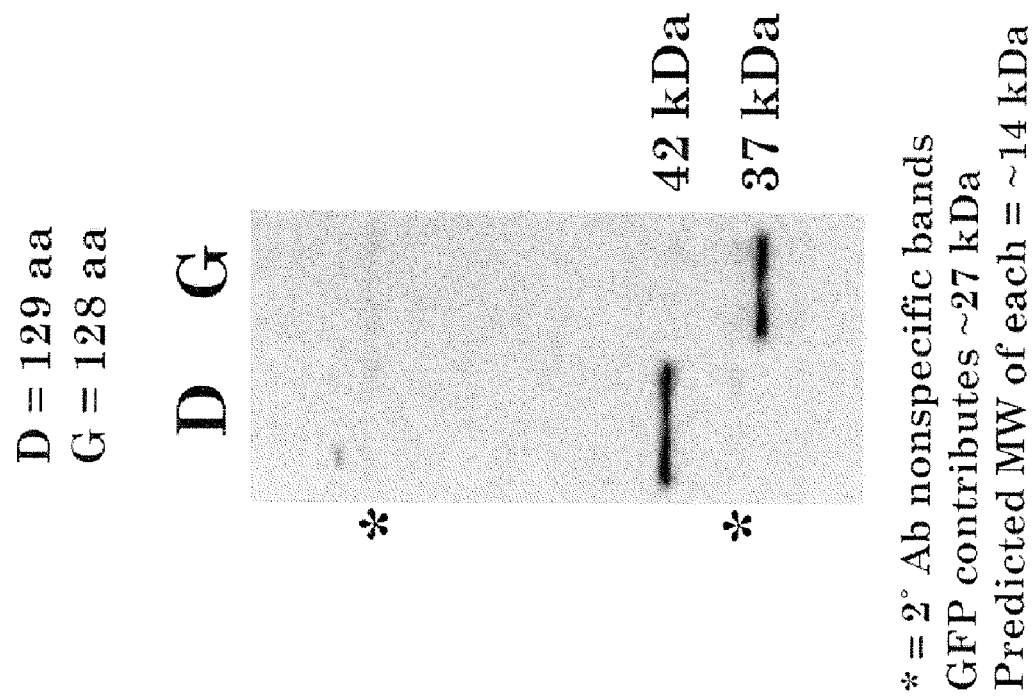
FIG. 15 provides the results of SDA-page analysis of DBD-D/GFP fusion protein and DBD-G/GFP fusion protein.

GFP fusion proteins including DBD-D or DBD-G polypeptides were analyzed by SDS-page gel electrophoresis. (See FIG. 15). The DBD-G domain fusion protein exhibited a faster migration pattern than the DBD-D domain fusion protein, which is characteristic of a basic polypeptide.

An RPA32 variant polypeptide was created in which the non-conserved region of DBD-D (i.e., amino acids 108-124 (SEQ ID NO:6) was replaced with the non-conserved region of RPA4 DBD-G (i.e., amino acids 108-123 (SEQ ID NO:3)). The variant was termed RPA32-basic (SEQ ID NO:7).

Figure 16:
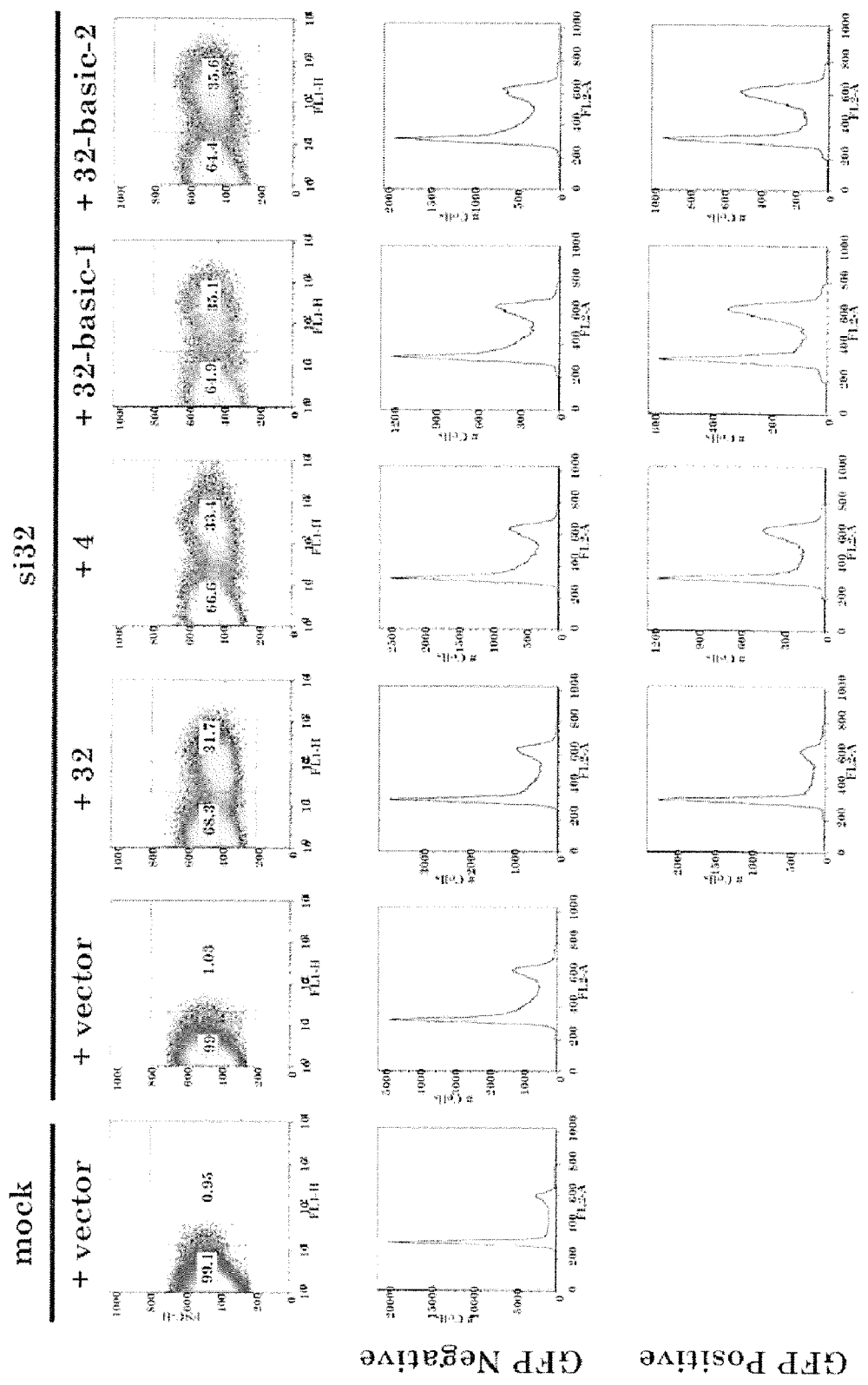
FIG. 16 illustrates cell cycle phenotype after RPA32 knockdown RPA32 expression, RPA4 expression, or RPA32-basic expression (performed in duplicate). As described in the Examples, HeLa cells were transfected with siRNA for RPA32 ("si32") and optionally transfected with RPA32 plasmid DNA ("+32"), RPA4 plasmid DNA ("+4"), or RPA32-basic DNA ("+32-basic-1" and "+32-basic-2"). Vector DNA was transfected as a control. The cell cycle phenotype was assessed by flow cytometry.
Figure 17:
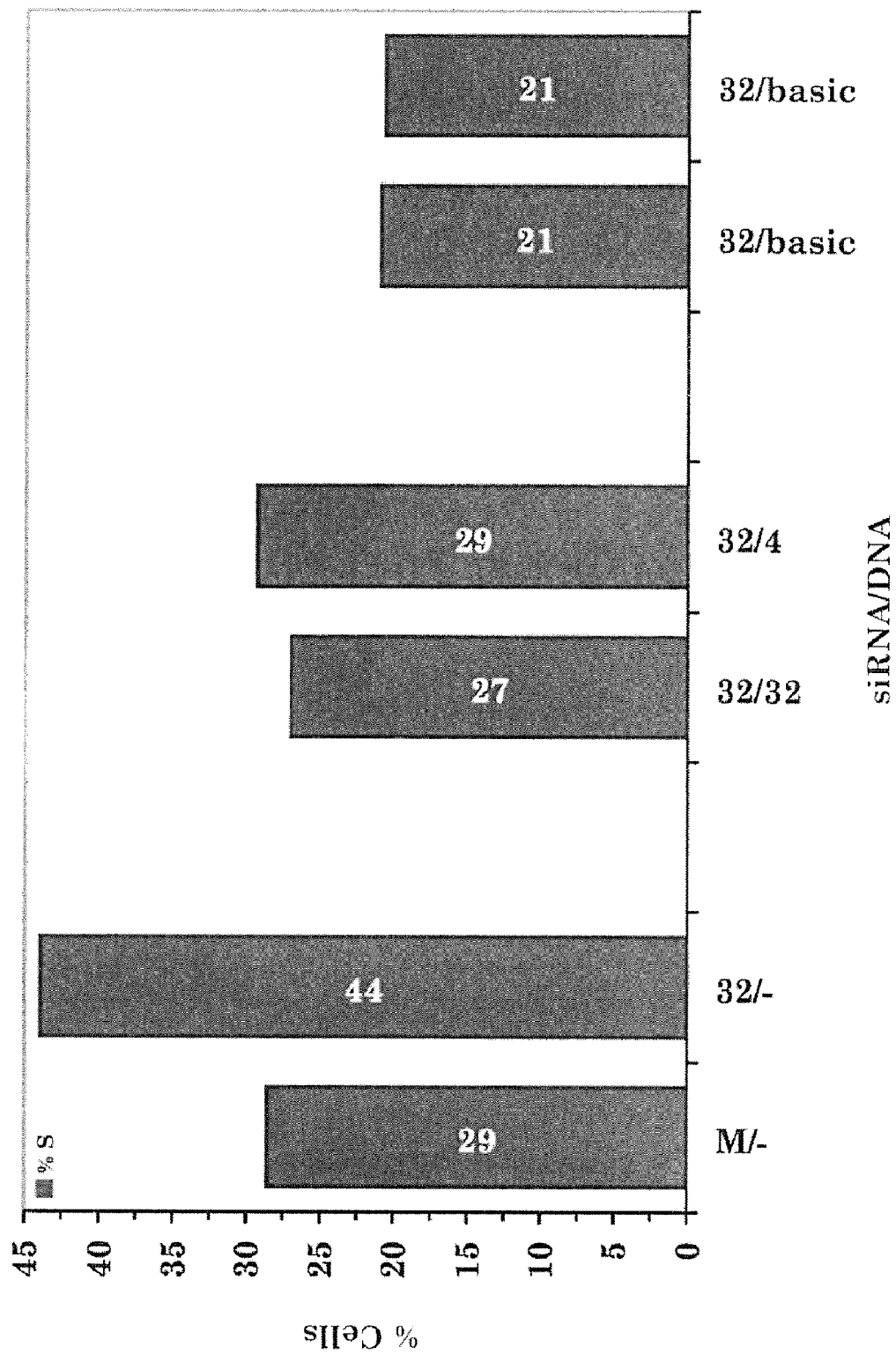
FIG. 17 illustrates the percentage of cells in S-phase after RPA32 knockdown and RPA32-basic expression. As described in the Examples, HeLa cells were transfected with siRNA for RPA32 ("32/", where "M/" designates mock-transfected cells), and optionally transfected with RPA32 plasmid DNA ("/32"), RPA4 plasmid DNA ("/4"), or RPA32-basic DNA ("/basic") in duplicate (where "/−" designates non-DNA-transfected cells). The cell cycle phenotype was assessed by flow cytometry.
Figure 18:
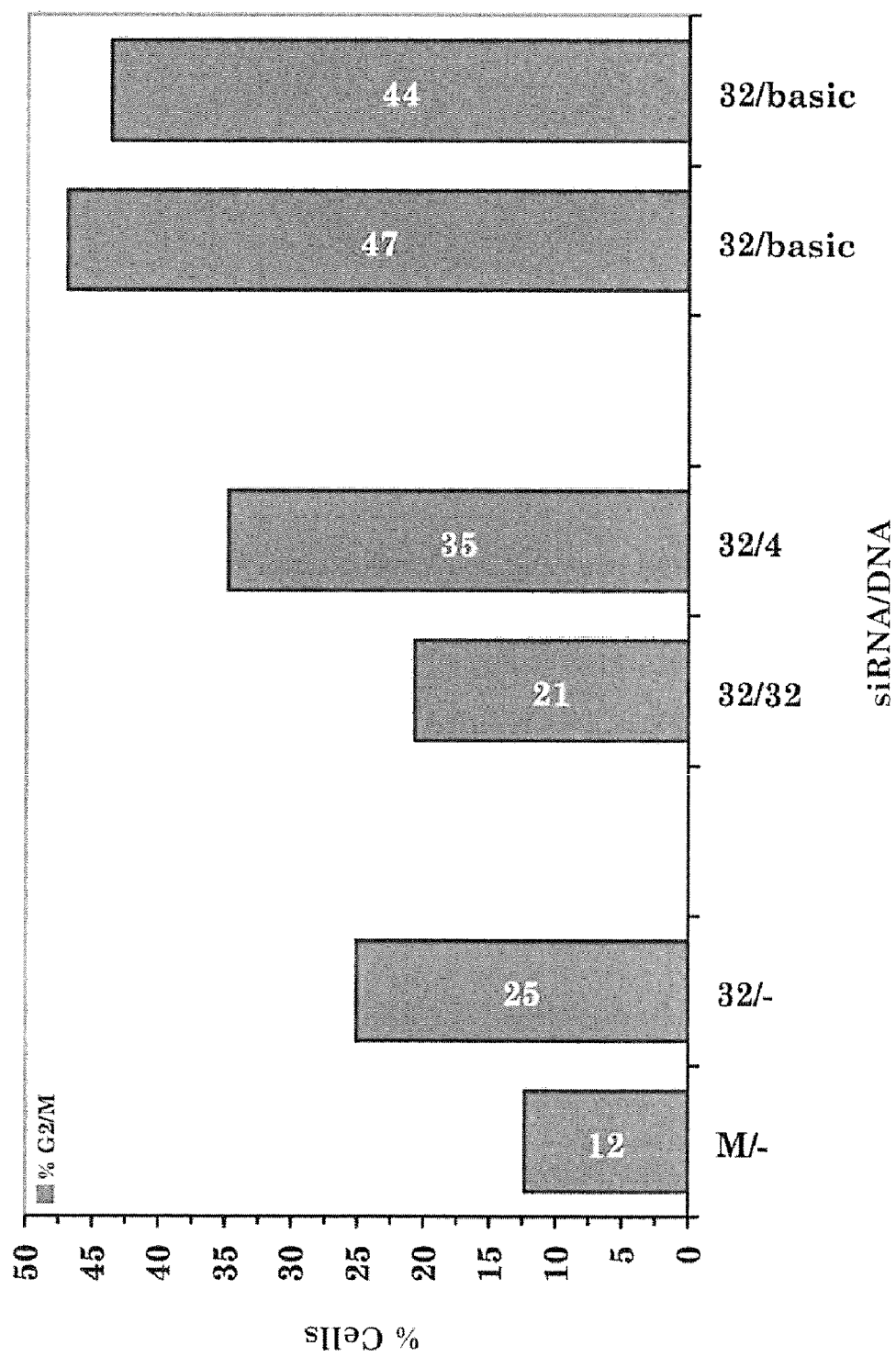
FIG. 18 illustrates the percentage of cells in G2/M-phase after RPA32 knockdown and RPA32-basic expression. As described in the Examples, HeLa cells were transfected with siRNA for RPA32 ("32/", where "M/" designates mock-transfected cells), and optionally transfected with RPA32 plasmid DNA ("/32"), RPA4 plasmid DNA ("/4"), or RPA32-basic DNA ("/basic") in duplicate (where "/−" designates non-DNA-transfected cells). The cell cycle phenotype was assessed by flow cytometry.
Figure 19:
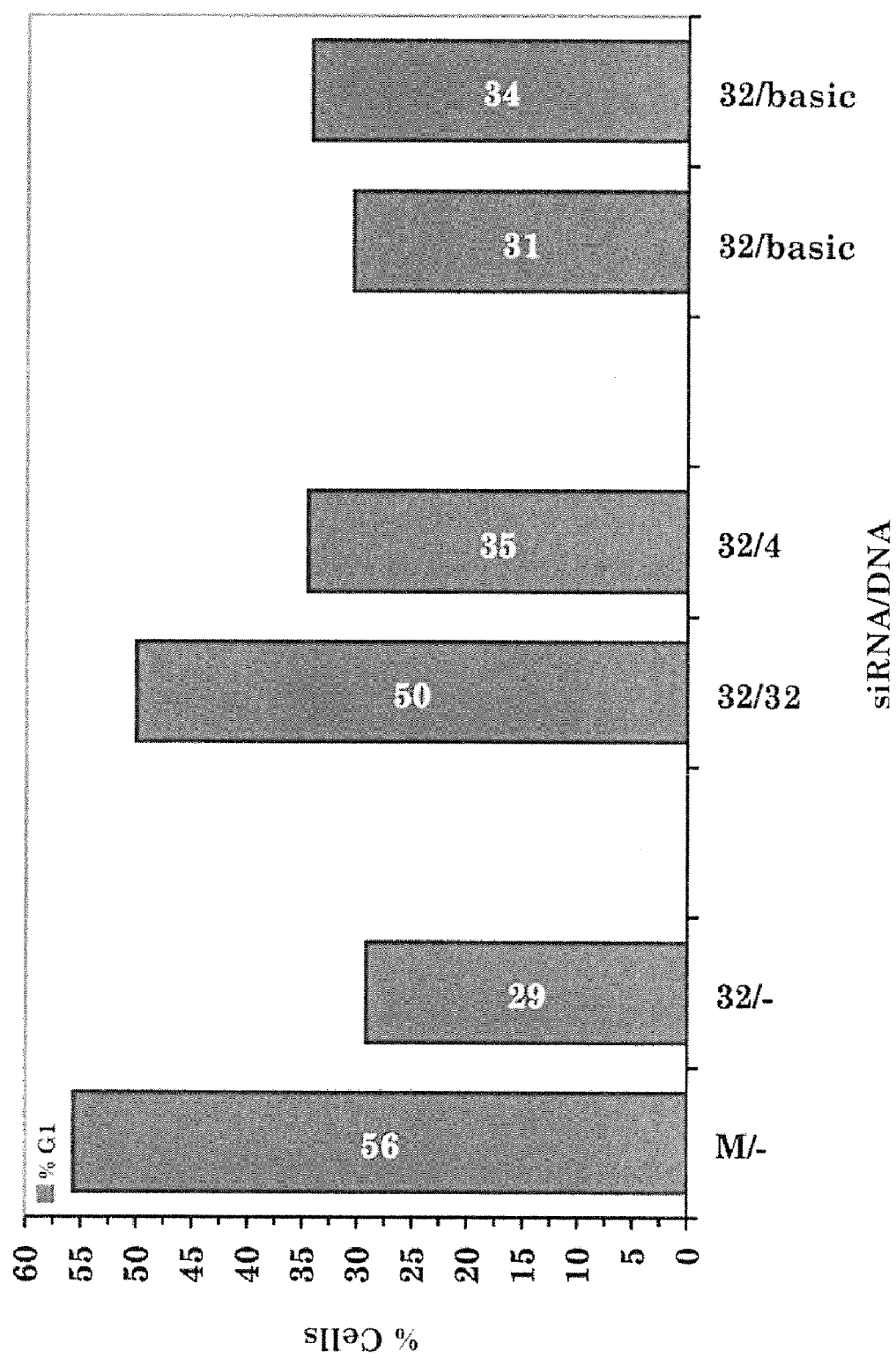
FIG. 19 illustrates the percentage of cells in G1-phase after RPA32 knockdown and RPA32-basic expression. As described in the Examples, HeLa cells were transfected with siRNA for RPA32 ("32/", where "M/" designates mock-transfected cells), and optionally transfected with RPA32 plasmid DNA ("/32"), RPA4 plasmid DNA ("/4"), or RPA32-basic DNA ("/basic") in duplicate (where "/−" designates non-DNA-transfected cells). The cell cycle phenotype was assessed by flow cytometry.

HeLa cells were transfected with small inhibitory RNA (siRNA) for RPA32 (i.e., si32) and subsequently were transfected in duplicate with DNA expression vectors for a GFP-RPA32-basic fusion polypeptide, or as controls, DNA expression vectors for a GFP-RPA32 fusion polypeptide or a GFP-RPA4 fusion polypeptide. The cell phenotype was analyzed by flow cytometry. (See FIG. 16.) Cells were sorted based on GFP expression. The results indicate that the RPA4 phenotype maps to the non-conserved basic region of DBD-G. The percentage of total cells in S-phase (FIG. 17), G2/M-phase (FIG. 18), or G1-phase (FIG. 19) was calculated. The results indicate that RPA32-basic expression can ameliorate the effects of RPA32 knockdown. However, RPA32-basic expression causes an accumulation of cells in G2/M-phase and RPA32-basic expression cannot restore cells to G1-phase. Point mutation at or near the acid loop region of RPA32 appear to affect cell cycle phenotype. Amino acid substitutions in RPA32 where acidic amino acids are exchanged for basic amino acids results in a phenotype similar to RPA4, where cells expressing the variants accumulate in G2/M-phase. The ability of a cell to proceed through the cell cycle may depend on the charge of the RPA32 polypeptide at or near the loop region of DBD-D.

VII. Complementation of RPA2 Knockdown by Exogenous Hybrids

Additional hybrid RPA2/RPA4 constructs were created and tested. A "cassettized" RPA2 was divided into three regions: the N-terminal phosphorylation domain (PD; aa 1-44), the central DNA binding domain (DBD-D; aa 45-172), and the C-terminal region (aa 173-270) containing a winged-helix domain (WHD). Each region of RPA2 was substituted with the corresponding region of RPA4. (See FIG. 20(a), which provides a schematic for hybrid constructs 422, 242, and 224).

The RPA2/RPA4 'hybrid' constructs were expressed and examined. All of the hybrid constructs were able to reduce the percentage of cells in S phase significantly (t-test;

0.0057<p<0.0305) compared to RPA4-expressing cells (FIG. 20(b)). Although the PD and WHD share the least sequence identity between RPA2 and RPA4, only the 242 hybrid construct containing the RPA4 DNA-binding domain RPA4 (DBD-G) displayed the other RPA4 phenotype, G2/M arrest (FIG. 20(b)).

In asynchronous cells, it appeared that exogenous RPA2 (WT) and hybrid constructs could rescue, to varying degrees, the replication defect due to RPA2-depletion, whereas RPA4 expression could not. To rule out the possibility that the observed depletion defect and rescue was due to some other phenomenon, cells were treated with the polymerase inhibitor aphidicolin (APH) to synchronize the cells at the G1/S boundary. FIG. 20(c) illustrates the results of rescue experiments in which cells with synchronized using aphidicolin (aphiphidocolin-blocked) and subsequently were released from the aphidicolin block. Cells were depleted for RPA2, treated with aphidicolin, collected after release, and examined by flow cytometry as described.

RPA4 and RPA(242) were not able to support S-phase progression. As expected, RPA2-depleted cells are unable to progress through S phase, whereas the exogenous RPA2-expressiong cells are proficient for DNA replication (FIG. 20(c)). The RPA4-expressing cells are clearly defective in replication, as indicated by the inability to progress through S phase (FIG. 20(c)). Of the hybrid constructs, 422 shows WT S phase progression, whereas 242 and 224 are less efficient (FIG. 20(c)). Given that the all of the hybrids rescue at least some of the replication defect, this would indicate that a combination of two or more of the RPA4 domains are necessary to inhibit replication to the same extent as RPA4.

It should be noted that although two hybrids (242 and 224) show reduced replication efficiency, only 242 demonstrated a G2/M arrest phenotype. This would suggest that the checkpoint activation is not due to defective DNA synthesis. As such, the ability of the hybrid constructs to participate in DNA damage recognition was assessed. Similar to RPA2 and RPA4, all of the hybrid constructs can also localize to DNA damage (data not shown), suggesting that there is no specific combination of RPA2/RPA4 domains necessary to recognize DNA damage.

VIII. Inhibition and Model for RPA4 Function in the Cell

Since RPA4 appears to be deficient in DNA replication but proficient for G2/M arrest, we addressed whether or not exogenous RPA4 expression could inhibit endogenous RPA2 function. To do this, cells were transfected with RPA2 or RPA4 without depletion of endogenous RPA2. A dominant negative phenotype should then be observed as either an increase in S phase cells due to replication deficiency, a G2/M checkpoint due to arrest proficiency, or both. We were unable to detect an appreciable increase in S phase or G2/M phase upon exogenous RPA4 expression (FIG. 21(a)).

Figure 21:
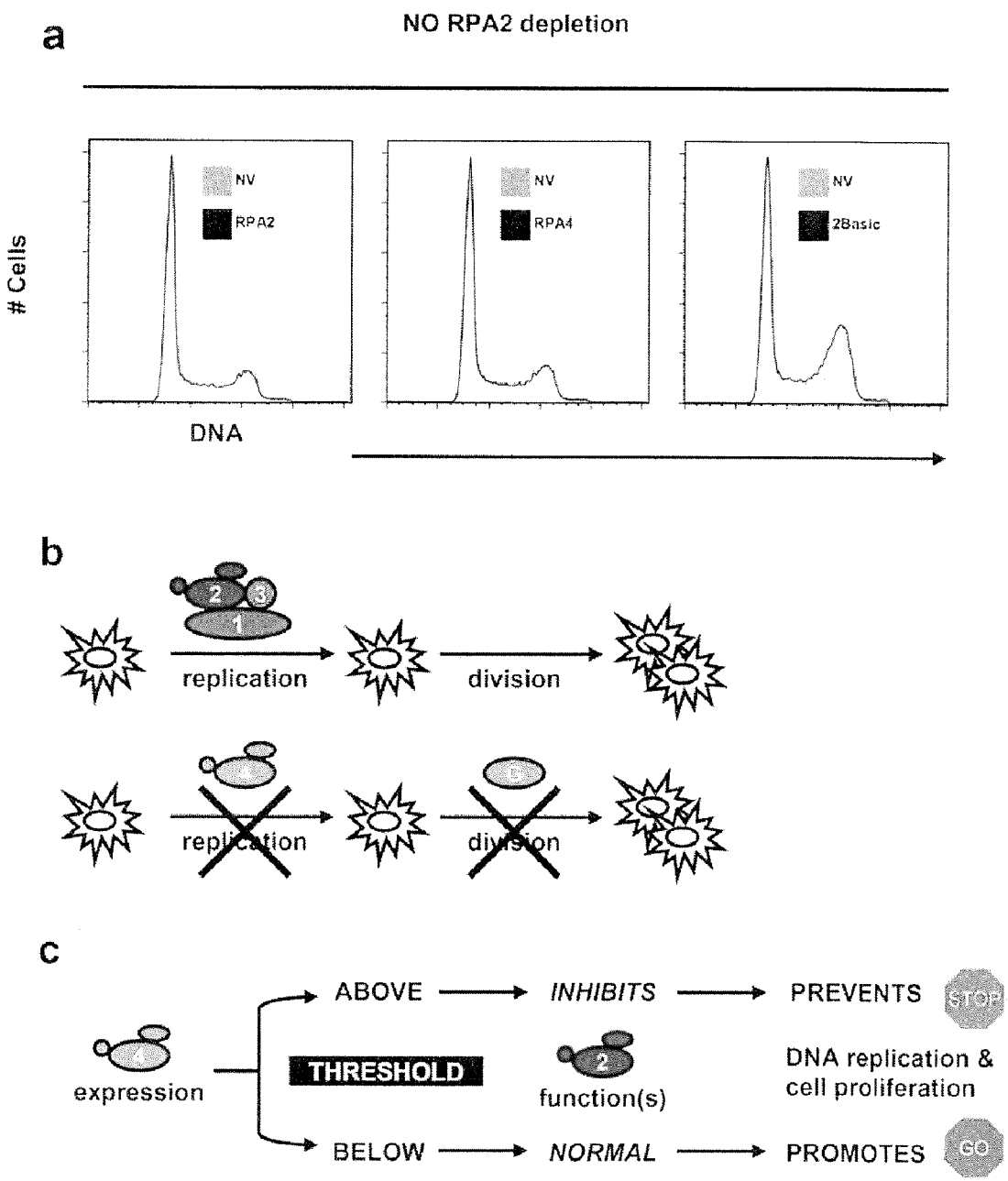
FIG. 21 provides an analysis and summary for RPA4 function in the cell: (a) Dominant negative analysis. In the presence of endogenous RPA2, exogenous RPA2, RPA4, and 2Basic were expressed. Overlays of the DNA histograms are shown. Black histograms represent cells with no vector (NV), and grey histograms represent cells expressing RPA2, RPA4, or 2Basic (otherwise referred to herein as "RPA32-basic"); (b) Summary of RPA4 expression in cells. Top half represents cell proceeding through the major events in the cell cycle (replication and division). Bottom half represents cells expressing RPA4; (c) Model for RPA4 function in the cell.

FIG. 21 provides an analysis for RPA4 function in the cell. FIG. 21(a) illustrates the results of a dominant negative analysis. In the presence of endogenous RPA2, exogenous RPA2, RPA4, and 2Basic (i.e., "RPA32-basic") were expressed. Overlays of the DNA histograms are shown. Black histograms represent cells with no vector (NV), and red histograms represent cells expressing RPA2, RPA4, or 2Basic. FIG. 21(b) provides a schematic summary of RPA4 expression in cells. The top half of the schematic represents cells proceeding through the major events in the cell cycle (replication and division). Functional RPA, containing RPA2 allows cells to replicate their DNA and proceed through the cell cycle. The bottom half of the schematic represents cells expressing RPA4. RPA4 cells are unable to proceed through replication and DBD-G causes an additional G2/M arrest, preventing cell division. FIG. 21(c) provides a model for RPA4 function in the cell. It is possible that RPA4 expression must reach a certain threshold to affect the cell. We propose that if expression is below the threshold, cells exhibit normal function (and likewise normal RPA2 function) and the ability to replicate DNA and divide. However, if RPA4 expression is above the threshold, it may inhibit normal RPA2 function, which would prevent DNA replication and would activate cellular processes necessary to halt the cell cycle.

There are a number of possible explanations for the absence of a dominant negative phenotype that include expression levels, protein stability, or complex preference. Interestingly, the RPA2-basic construct, which contains the L34 region (only 16 aa) of RPA4, construct did result in a detectable increase in G2/M arrested cells (FIG. 21(a)). This is consistent with the results that demonstrate that a complex containing RPA2-basic is able to inhibit WT RPA replication function in vitro.

It appears that RPA4 is deficient or prevents DNA replication, and that DBD-G also prevents cell cycle progression by G2/M arrest. (See FIG. 21(b)). An interesting observation is that RPA4 was originally found to be expressed in colon mucosal cells, which were noted to be mostly nonproliferative; however, in colon cancer, RPA2 expression is increased and correlated with the severity of the cancer. Keshav et al., supra, noted that RPA4 is detected in primarily quiescent cells and suggested that preferential expression of RPA4 vs. RPA2 may be indicative of tissue differentiation and entry of cells into quiescence. Our studies are consistent with this idea and indicate that expression of RPA4 is having a direct causal effect that may promote proliferating cells to become quiescent, by its ability in inhibit DNA replication and by the prevention of cell cycle progression. This is the first examination of RPA4 function in the cell, and we propose that expression of RPA4 may be a cellular mechanism used to halt cell proliferation and has implications as a potential therapeutic strategy in the prevention of abnormal cell growth.

IX. Expression of RPA4 in Cancerous Tissue as Compared to Normal Tissue

Rpa4 mRNA is found in normal human tissues. The initial characterization of RPA4 by Keshav et al. examined three human tissues for the presence of RPA4 protein. (See Keshav et al., (1995) Mol. Cell. Biol. 15, 3119-3128.) They showed that RPA4 protein was detectable in placental and colon tissue but not in kidney. If RPA4 is playing a general physiological role in cellular DNA metabolism, it would be expected to be expressed in a variety of tissues. To determine the normal distribution of RPA4, mRNA expression in a panel of human tissues was determined by quantitative PCR.

Figure 22:
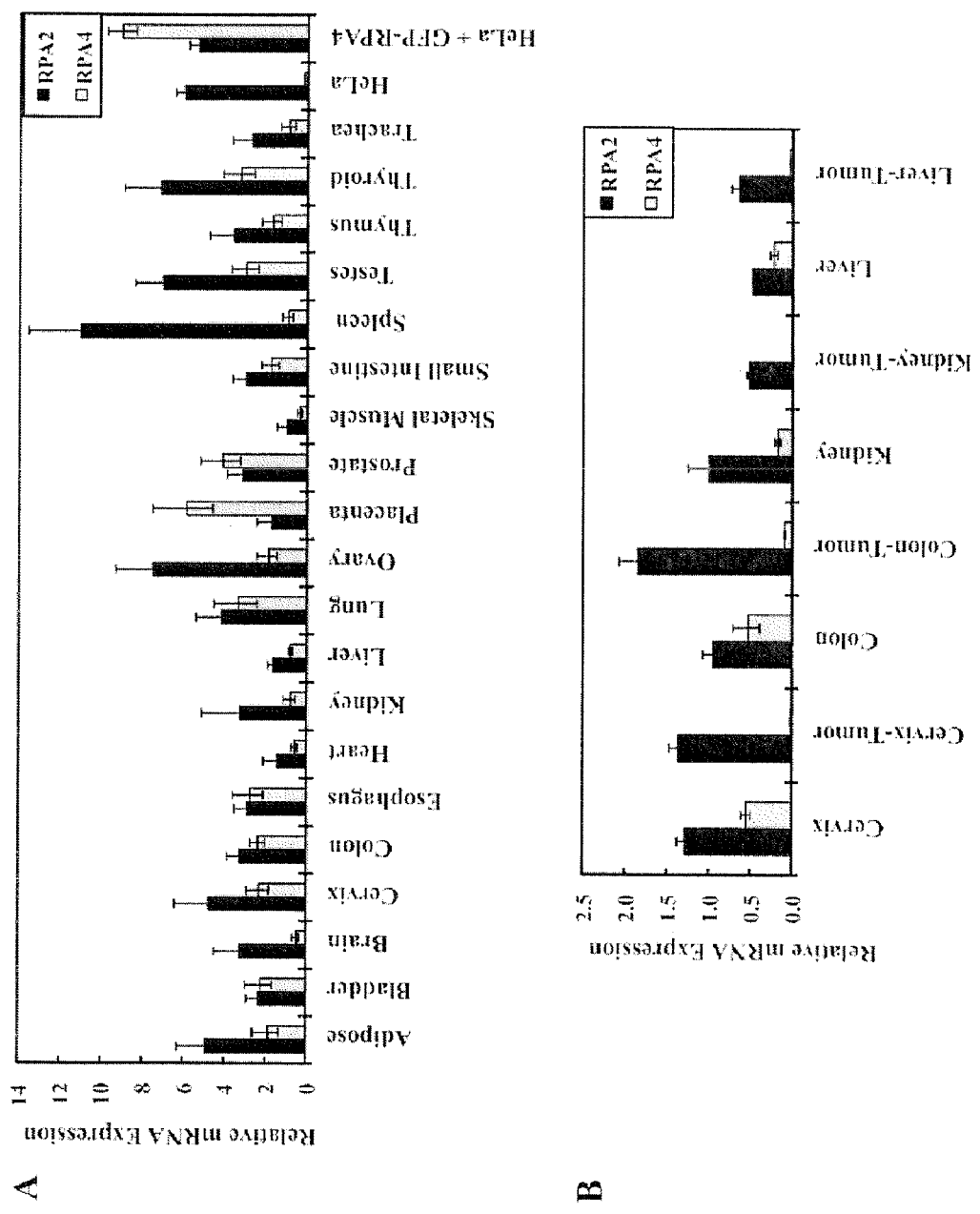
FIG. 22 illustrates quantitative PCR of RPA4 and RPA2 mRNA. Relative mRNA expression of RPA2 (black) and RPA4 (grey) as determined by the comparative Ct method. Error bars indicate the average of three technical and two experimental replicates. A. cDNA was made from a panel of 20 normal human tissues (Ambion), HeLa cells either mock-transformed and HeLa cells transformed with GFP-RPA4 fusion protein under the control of the CMV promoter. (See Haring et al., Nucleic Acids Res. 2009 Nov. 26 [Epub ahead of print]). B. cDNA made from normal and tumor tissue samples (Ambion).

Since it was not known which tissues normally express Rpa4, initial studies were carried out on HeLa cells transiently expressing a plasmid containing Rpa4 under control of a CMV promoter. These cells express RPA4 protein at high levels. (See Haring et al., Nucleic Acids Res. 2009, Nov. 26, 1-1-13 [Epub ahead of print]). PCR amplification of cDNA from untransfected and transfected HeLa cells was compared. Messenger RNA levels for Rpa2 and Rpa4 were then compared using GAPDH as a reference. HeLa cells transfected with the Rpa4 plasmid express Rpa4 at levels greater than endogenous Rpa2 (FIG. 22A, right two columns). In contrast, mock-transfected HeLa cells that do not have an appreciable amount of Rpa4 mRNA (FIG. 22A). The endogenous level of RPA4 mRNA is close to the level of detection of this assay and may not be statistically significant. We also examined expression of other stable human cell lines (including for example HEK-293 and HepG2) and did not find significant expression of Rpa4 in any of the lines tested (data not shown).

RNA from 20 different tissues was analyzed for Rpa2 and Rpa4 expression. In agreement with the protein studies by Keshav and coworkers ((1995) Mol. Cell. Biol. 15, 3119-3128), Rpa4 mRNA was detected at levels above Rpa2 mRNA in placental tissue (FIG. 22A). Rpa4 mRNA was also detected at levels similar to or above Rpa2 mRNA in a number of tissues including bladder, colon, esophagus, lung and prostate. In other tissues, Rpa4 was expressed at levels less than 20% of the total middle subunit mRNA (Rpa2 mRNA+Rpa4 mRNA) include brain, kidney, ovary and spleen (FIG. 22A). The remaining tissues expressed Rpa4 at intermediate levels. These results are consistent with an initial analysis of RPA4 protein levels in placenta and colon tissues (data not shown) and the analysis performed by Keshav and coworkers ((1995) Mol. Cell. Biol. 15, 3119-3128). Similar variations were observed for Rpa2 mRNA (FIG. 22A). For example, heart, liver and skeletal muscle all have low amounts of RPA2 mRNA compared to ovary, spleen, testes and thyroid, which have the most RPA2 mRNA in the tissues sampled. We conclude that all normal tissues examined transcribe Rpa4 at significant levels and, although there is tissue specific variation, in many tissues Rpa4 mRNA levels are comparable to the Rpa2 mRNA.

To determine whether Rpa4 was also expressed in cancerous tissues, RNA from several types of tumors was examined. Rpa4 mRNA was expressed at reduced levels in tumors from cervix, colon, kidney and liver when compared to non-matched normal tissue (FIG. 22B). In three out of the four tissues compared, the levels of Rpa2 mRNA increased. This is in agreement with the literature that has found increased expression of RPA in metastatic cancers. (See Givalos et al., (2007), Mod. Pathol. 20, 159-166; and Tomkiel et al., (2002) Clin Cancer Res. 8, 752-758). These data, together with the finding that RPA4 is not expressed at significant levels in stable cultured cell lines suggests that RPA4 is down regulated in transformed cells. This supports the hypothesis that RPA4 plays a role in normal tissues but not in tissues with a large fraction of proliferating cells.

Methodology

I. Exogenous RPA Expression Constructs

To identify exogenous expression of RPA in HeLa cells, enhanced green fluorescent protein (EGFP)-tagged RPA1, RPA2, RPA3, and RPA4 constructs were generated. To generate EGFP-RPA1 (pEGFP-hsRPA1) and EGFP-RPA3 (pEGFP-hsRPA3), the respective coding regions were PCR amplified from p11d-tRPA and inserted into the BglII-KpnI sites of pEGFP-C1 (Clontech). To generate EGFP-RPA2 (pEGFP-hsRPA2), the RPA2 coding region was PCR amplified from p11d-tRPA and inserted into the XhoI-KpnI sites of pEGFP-C1. EGFP-RPA4 (pEGFP-hsRPA4) was generated by PCR amplification of the RPA4 coding region from pBABE-puro-RPA4 and inserted into the BglII-KpnI sites of pEGFP-C1. All constructs were confirmed by sequencing.

RPA2/RPA4 hybrid constructs were generated by first creating a 'cassettized' EGFP-RPA2 construct (pEGFP-hsRPA2-AS). A unique AflII site was generated between the phosphorylation domain and the DNA binding domain using the QuikChange XL Site-Directed Mutagenesis Kit (Stratagene). A unique SpeI site was generated between the DNA binding domain and the C-terminal region containing the winged-helix domain using the QuikChange XL Site-Directed Mutagenesis Kit. PCR was used to amplify the putative phosphorylation domain, the putative DBD domain, or the C-terminal region of RPA4, and these fragments were used to replace the corresponding domain of RPA2.

II. Cell Lines and Tissue Culture

HeLa cells were grown in Dubelcco's Modified Eagle's Medium (DMEM) supplemented with 10% bovine calf serum (BCS) at 37° C. and 5% $CO_2$.

III. RNA Interference (RNAi) and Exogenous RPA Expression

Small interfering RNA (siRNA) targeting the 3' untranslated region (UTR) of RPA2, RPA1, or RPA3 mRNA were generated (Dharmacon).

HeLa cells were seeded in six-well tissue culture plates at $2 \times 10^5$ cells/well for 18-24 hr. Cells were then transfected with 200 pmol siRNA using Lipofectamine 2000 (Invitrogen); this is time zero (t=0). At 24 hr post-transfection of siRNA (t=24), the media was removed from the cells and fresh DMEM/10% BCS was added to each well. The cells were then transfected with 250 ng of the appropriate plasmid DNA using Lipofectamine 2000. At 48 hr post-transfection of siRNA (t=48), the media was removed and fresh DMEM/10% BCS was added to the cells. The cells were then grown until collected for protein, immunofluorescence (IF), or flow cytometry.

IV. Induction of DNA Damage

To examine the localization of RPA to DNA damage foci, HeLa cells were treated as described for RNAi above, except that at 90 hr post-transfection of siRNA, camptothecin was added to each well to a final concentration of 2 μM. The cells were incubated for 4 hr and subsequently prepared for fluorescence microscopy. RPA4 was observed to localize at nuclear foci in the cell.

To examine the ability to establish the G2/M checkpoint, HeLa cells were treated as described for RNAi above. At t=48, camptothecin was added to a final concentration of 0.03 μM, and the cells were subsequently collected at t=90 for flow cytometric analysis.

V. Cell Lysates and Protein Detection

Cells were collected at various times post-transfection and pelleted at 1.5 rcf for 2 min. The cells were washed in PBS and pelleted at 1.5 rcf for 2 min. Cells were then resuspended/lysed in RIPA buffer and placed at −80° C. Cell lysates were thawed, sonicated with a microtip at setting 4 using a Fisher sonicator by pulsing for 5 sec four times, and the protein was quantitated using the Bio-Rad DC assay. Equal amounts (100 μg) of protein were loaded on an 8-14% gradient SDS-PAGE gel and run at 40 W for 1.5-2 hr. Gels were electroblotted onto Bio-Rad nitrocellulose membrane at 0.2 mA for 16-20 hr at 4° C.

VI. Cell Cycle Analysis by Flow Cytometry

RNAi and transfection of plasmid DNA were performed as described for knockdown and exogenous expression above. At various times following RNAi knockdown, the media from each well was collected, and the remaining attached cells were trypsinized. The trypsinized cells and collected media were combined and pelleted at 1.25 g for 3 min at room temperature (RT). The cells were washed once with PBS and fixed and permeabilized 1 hr to overnight in 70% methanol. The fixed cells were pelleted at 1.25 g for 3 min, and 1 mL of PBS was added to each tube. The cells were incubated at RT for 1-2 hr. The rehydrated cells were pelleted at 1.25 g for 3 min and 150 μL of RNaseA solution (X mg/mL RNase in PBS) was added to each tube, and the cells were incubated at 4° C. for 1-2 hr. Finally, 150 μL of propidium iodide (PI) solution (X mg/mL PI in PBS) was added to each tube. Cells were examined within 1-3 days on a Becton Dickinson FACSCalibur using FlowJo software (TreeStar). Quantitation of the cell cycle was performed using the Cell Cycle analysis tool in FlowJo.

VII. Quantitative Nucleic Acid Detection

Quantitative PCR-RNA from cell lines was isolated using Qiagen RNeasy Mini Kit according to manufacturer's protocol. Normal human RNA was purchased from Ambion as the FirstChoice Human Total RNA Survey Panel and tumor RNA was purchased from Ambion as FirstChoice Human Tumor RNA. cDNA was generated using TaqMan Reverse Transcription Reagents according to manufactures protocol using oligo d(T)$_{16}$ and 2 µg total RNA in a 20 µL RT reaction.

Quantitative PCR was carried out using TaqMan Universal PCR Master Mix according to manufactures recommendations using the following primers and probes: GAPDH-primers: 5'-GCACCACCAACTGCTTAGCA-3' (SEQ ID NO:15), 5'-GTCTTCTGGGTGGCACTGATG-3' (SEQ ID NO:16); probe: 5'-TET--TCGTGGAAGGACTCATGAC-CACAGTCC (SEQ ID NO:17) -Black Hole Quencher -3'; RPA2-primers: 5'-TTGTTTGAAGCTCAGAGGGAGAT-3' (SEQ ID NO:18), 5'--GGTAGCATCCTTCCAATTCCAT-3' (SEQ ID NO:19); probe: 5'-6-FAM-CCCACCCTGGATTG-CATCCC (SEQ ID NO:20) -Black Hole Quencher-3'; RPA4-primers: 5'-CTCATCAGGAAGGGAAGAGCAT-3'; (SEQ ID NO:21), 5'--GCCCTCAACGGTCAGATAATCA-3' (SEQ ID NO:22); probe: 5'-JOE NHS Ester-AGCTC-CGGGCTCAGCTCTGC (SEQ ID NO:23) -Black Hole Quencher-3'. Data was analyzed using SDS2.3 software by Applied Biosystems. All data was compared using the comparative $C_T$ method. (See Pfaffl, M. W. (2001) Nucleic Acids Res. 29, e45). All probes pairs amplify their target with equal efficiency (data not shown).

All patent and non-patent references cited in this specification are herein incorporated by reference as if each individual reference were specifically and individually indicated to be incorporated by reference. In the event that there is an inconsistency between a definition of a term in the specification as compared to a definition of the term in a cited reference, the term should be interpreted based on the definition in the specification.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification or variation of the concepts herein disclosed may be resorted to by those skilled in the art, and that such modifications and variations are considered to be within the scope of this invention.

We claim:

1. An isolated polynucleotide comprising a coding sequence for an replication protein A 32 (RPA32) variant polypeptide having at least 96% amino acid sequence identity to SEQ ID NO:7, wherein the polypeptide binds to at least one of replication protein A 1 (RPA1) and replication protein A 3 (RPA3).

2. The isolated polynucleotide of claim 1, wherein the encoded Polypeptide comprises SEQ ID NO:7.

3. The isolated polynucleotide of claim 1, wherein the encoded Polypeptide forms a complex with RPA1 and RPA3.

4. The isolated polynucleotide of claim 1, wherein the encoded Polypeptide binds single stranded nucleic acid.

5. The isolated polynucleotide of claim 1, wherein the encoded Polypeptide inhibits proliferation of human cells.

6. The isolated polynucleotide of claim 1, wherein the encoded Polypeptide comprises SEQ ID NO:3.

7. The isolated polynucleotide of claim 6, wherein the encoded Polypeptide comprises SEQ ID NO:3 at a region from amino acid 108 to amino acid 123 of the encoded polypeptide.

8. The isolated polynucleotide of claim 1, wherein the polypeptide Comprises two or more basic amino acid residues within a region from amino acid 108 to amino acid 123 of the encoded polypeptide.

9. The isolated polynucleotide of claim 1, wherein the polypeptide does not comprise more than one acidic amino acid residue within a region from amino acid 108 to amino acid 123 of the polypeptide.

10. The isolated polynucleotide of claim 1, wherein the polypeptide comprises a domain from a replication protein selected from the group consisting of a phosphorylation domain; a DNA binding domain; a winged-helix domain; and combinations thereof.

11. A recombinant polynucleotide comprising a promoter sequence operably linked to the polynucleotide of claim 1.

12. An isolated cell transformed with the recombinant polynucleotide of claim 11.

13. A vector comprising the recombinant polynucleotide of claim 11.

* * * * *